United States Patent
Li

(10) Patent No.: US 7,838,249 B2
(45) Date of Patent: Nov. 23, 2010

(54) ASSAYS FOR RAB5 ACTIVITY

(75) Inventor: Guangpu Li, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 11/998,244

(22) Filed: Nov. 29, 2007

(65) Prior Publication Data

US 2008/0145865 A1    Jun. 19, 2008

Related U.S. Application Data

(60) Provisional application No. 60/861,619, filed on Nov. 29, 2006.

(51) Int. Cl.
*G01N 33/53* (2006.01)
(52) U.S. Cl. .................. 435/7.1; 435/7.2; 435/7.91; 435/7.92
(58) Field of Classification Search .................. None
See application file for complete search history.

(56) References Cited

U.S. PATENT DOCUMENTS

2005/0014206 A1*   1/2005  Vodermaier et al. ........ 435/7.21

OTHER PUBLICATIONS

Stetnmark et al. (Cell 1995, vol. 83, p. 423-432).*
Colman et al in Research in Immunology (145(1):33-36, 1994.*
Abaza et al in Journal of Protein Chemistry (11(5):433-444, 1992).*
Lederman et al in Molecular Immunology (28:1171-1181, 1991).*

* cited by examiner

*Primary Examiner*—Jacob Cheu
(74) *Attorney, Agent, or Firm*—Dunlap Codding, P.C.

(57) ABSTRACT

Methods of determining intracellular levels of Rab5 activity are disclosed, as well as fusion proteins utilized in such methods and recombinant constructs encoding such fusion proteins. The fusion protein contains a Rab5-binding domain that specifically binds to an activated form of Rab5-GTP, and a tag conjugated thereto, wherein the tag binds to an affinity matrix for purification of Rab5-GTP. Also disclosed are kits for determining intracellular levels of Rab5 activity.

14 Claims, 15 Drawing Sheets
(7 of 15 Drawing Sheet(s) Filed in Color)

ASSAYS FOR RAB5 ACTIVITY

CROSS REFERENCE TO RELATED APPLICATIONS

This application claims benefit under 35 U.S.C. 119(e) of U.S. Ser. No. 60/861,619, filed Nov. 29, 2006; the contents of which is hereby expressly incorporated herein by reference in its entirety.

STATEMENT REGARDING FEDERALLY SPONSORED RESEARCH AND DEVELOPMENT

Not Applicable.

BACKGROUND OF THE INVENTION

The Ras-related GTPase superfamily contains a large number of 20-30 kDa proteins, including the Ras, Rho/Rac, Ran, ADPribosylation factor ('ARF') and Rab proteins. They cycle between GTP-bound and GDP-bound conformations and thereby regulate diverse cellular functions such as signal transduction, cytoskeleton organization and intracellular trafficking.

The Rab family of proteins is a member of the Ras superfamily of GTPases, or enzymes that can bind and hydrolyze Guanosine triphosphate (GTP). Approximately 70 types of Rabs have now been identified in humans. Some types of Rabs are involved in the release of neurotransmitters from synaptic vesicles.

Like other members of the Ras superfamily, Rab proteins cyclically transmit signals to downstream effectors in a guanine-nucleotide-dependent manner. In the cytosol, Rab proteins are maintained in the GDP-bound form complexed to Rab GDI (GDP dissociation inhibitor). Upon membrane association, whereas Rab GDI dissociates and is released in the cytosol, the inactive Rab protein is converted into the GTP-bound active form by GDP/GTP exchange factors (GEFs). The switch between the GDP- and GTP-bound state is essential because it determines the ability to regulate the vesicle transport machinery.

Once Rab proteins are bound to a vesicle surface, they can be activated by the replacement of guanosine diphosphate with GTP, and this exchange is catalyzed by guanine nucleotide exchange factors, or GEFs. Rabs bound to GTP are in the active conformation and can now interact with or recruit Rab effectors on target membranes within the cell. Binding of Rab to a Rab effector tethers the vesicle to its appropriate target membrane and allows other membrane surface proteins to interact, resulting in the docking of the vesicle to the target membrane. Now the Rab has fulfilled its function and the GTP is degraded to GDP (catalyzed by GTPase-activating proteins, or GAPs). The Rabs can then be recycled back to their membrane of origin. The GDP dissociation inhibitor (GDI) is necessary for the recycling pathway. This enzyme binds the prenylated Rab, inhibits the exchange of GDP for GTP (which would reactivate the Rab), solubilizes the prenyl groups, and delivers the Rab to its original membrane. GDI and REP proteins have related functions and are related enzymes. The fraction of GTP-bound Rab5 on the membrane is thus rate limiting for endosome dynamics.

Endocytosis is the process mammalian cells utilize for the uptake of essential molecules from their external environment. This material is taken into cells by membranous vesicles derived from the plasma membrane (endocytic vesicles), and once internalized, it is directed to a system of internal vesicles called endosomes. In endosomes a number of important sorting events are carried out and include the separation and segregation of the material taken into the cell from the components of the endocytic vesicle. The latter components are returned (recycled) to the plasma membrane for use in subsequent rounds of endocytosis, whereas the endocytosed material is mostly sorted into lysosomes. The endosomal system is composed of a series of distinct elements, some of which are thought to perform sorting (rab5-positive endosomes) or recycling (rab11-positive endosomes) activities. Late endosomes (rab7-positive endosomes) appear to participate in routing material destined for degradation from the rab5-positive sorting compartment to the lysosomal compartment.

Rab5 is a small GTPase localized on early endosomes, and Rab5 controls early endosome fusion along the endocytic pathway. Rab5 functions as a molecular switch regulating endocytosis by facilitating early endosome fusion and possibly the budding of endocytic vesicles from the plasma membrane as well. Overexpression of Rab5 in cultured cells stimulates endocytosis. For newly synthesized Rab5 molecules to obtain biological activity, they first need to be modified by isoprenylation, then escorted to endosomal membranes where they undergo nucleotide exchange to become the active GTP-bound conformation. These processes have been suggested to be facilitated by Rab5-specific membrane recruitment machinery and a guanine nucleotide exchange factor. The activated Rab5 recruits effectors to promote the docking of endosomes, which ultimately leads to membrane fusion.

A number of different cytosolic factors have been identified in mammalian cells that are effector molecules that interact with Rab proteins with specificity for the triphosphate conformation. While it is intriguing that all these proteins share no detectable sequence homology, they all appear to be soluble factors that can be recruited on the membrane by the active form of Rab proteins. Examples of such molecules which act as effectors for Rab5 include, but are not limited to, Rabaptin-5, EEA1 (early endosome autoantigen), APPL1 and APPL2 (adaptor protein containing PH domain, PTB domain, and Leucine zipper motif 1 or 2), and Rabenosyn-5.

Prior to the present invention, the only way to determine Rab5 activity in a cell was to label the cell with [$^{32}$P]orthophosphate, followed by immunoprecipitation with Rab5 antibodies, thin-layer chromatography, and autoradiography. This is a difficult procedure that requires a lengthy amount of time (at least 6 hours) to complete, and also utilizes hazardous radioactive reagents.

Therefore, new and improved methods of determining intracellular Rab5 activity are being sought that are faster, easier to perform and safer than the prior art methods. It is to such assays that the present invention is directed.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
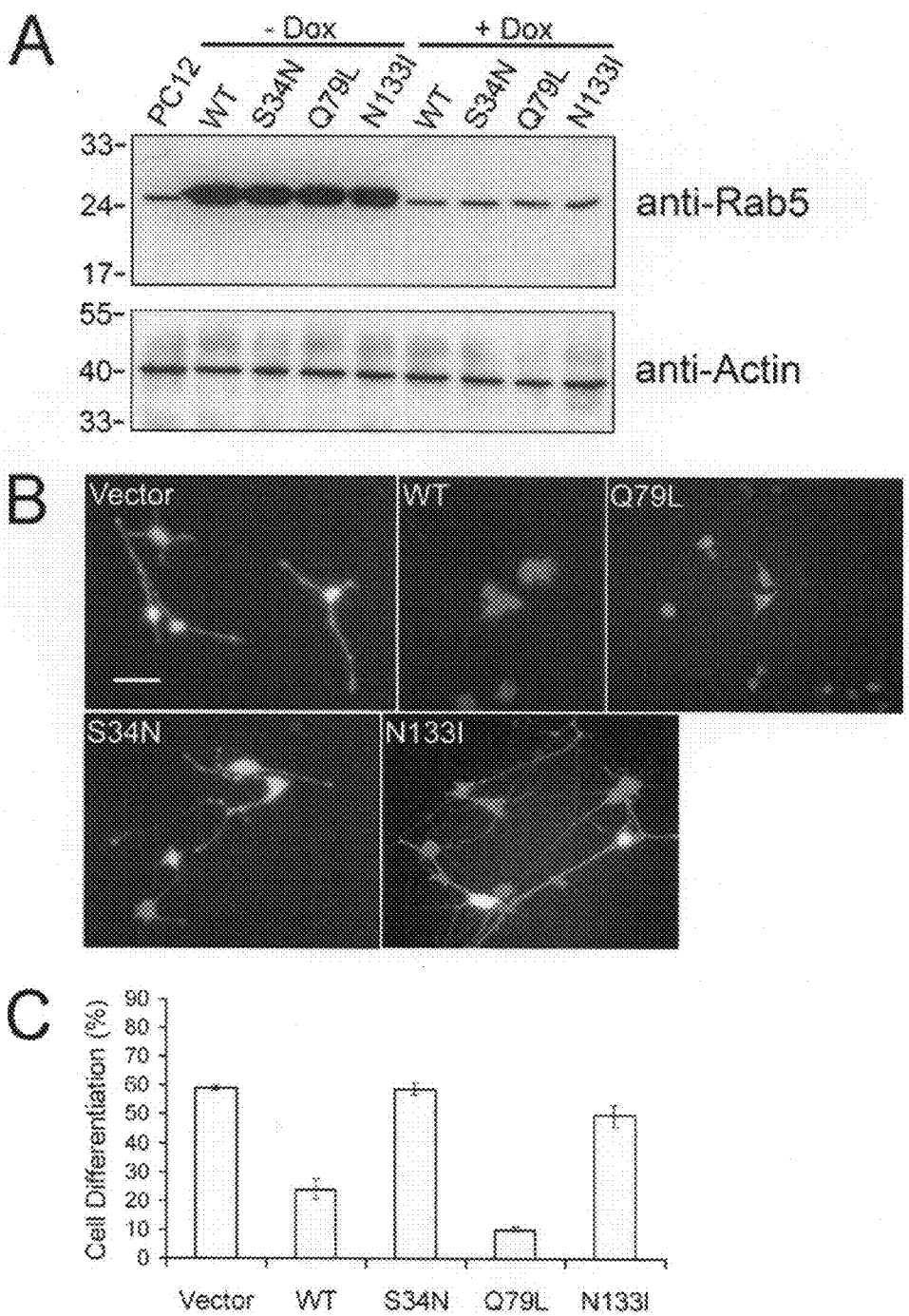
FIG. 1 illustrates neurite outgrowth in PC12 cells transfected with Rab5 mutants in response to NGF treatment. (A) Immunoblot analysis of the expression of the indicated Rab5 proteins in the absence or presence of 1 μg/ml Dox. Top, expression levels of the transfected Rab5 constructs (WT, Q79L, and S34N) as detected by the anti-Rab5 antibody. Bottom, actin level in each sample as the loading control (anti-actin). Lane PC12 shows endogenous levels of Rab5 or actin in cells transfected with the empty vector. Molecular mass standards are indicated on the left (in kilodaltons). (B) Fluorescence microscopy images of the cells after a 6-d treatment with 50 ng/ml NGF. Cells were transfected either with the empty pBI/EGFP vector (vector) or with constructs expressing the indicated Rab5 proteins. Bar, 50 μm. (C) Quantification of PC12 cell differentiation upon expression of WT and mutant Rab5 proteins. Percentage of differentiated cells with extended neurites was determined among the transfected cells expressing EGFP and thus the indicated WT or mutant Rab5 proteins. In each case, the total number of transfected cells measured is as follows: vector, >100; WT, >80; S34N, >80; Q79L, >80; and N133I, >100. Error bars represent SEM of three independent experiments.

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art.

As utilized in accordance with the present disclosure, the following terms, unless otherwise indicated, shall be understood to have the following meanings:

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a coding sequence isolated away from, or purified free from, unrelated genomic DNA, genes and other coding segments. Included within the term "DNA segment", are DNA segments and smaller fragments of such segments, and also recombinant vectors, including, for example, plasmids, cosmids, phage, viruses, and the like. In this respect, the term "gene" is used for simplicity to refer to a functional protein-, polypeptide- or peptide-encoding unit. As will be understood by those in the art, this functional term includes genomic sequences, cDNA sequences or combinations thereof. "Isolated substantially away from other coding sequences" means that the gene of interest forms the significant part of the coding region of the DNA segment, and that the DNA segment does not contain other non-relevant large portions of naturally-occurring coding DNA, such as large chromosomal fragments or other functional genes or DNA coding regions. Of course, this refers to the DNA segment as originally isolated, and does not exclude genes or coding regions later added to, or intentionally left in, the segment by the hand of man.

Preferably, DNA sequences in accordance with the present invention will further include genetic control regions which allow the expression of the sequence in a selected recombinant host. The genetic control region may be native to the cell from which the gene was isolated, or may be native to the recombinant host cell, or may be an exogenous segment that is compatible with and recognized by the transcriptional machinery of the selected recombinant host cell. Of course, the nature of the control region employed will generally vary depending on the particular use (e.g., cloning host) envisioned.

Truncated genes also fall within the definition of preferred DNA sequences as set forth above. Those of ordinary skill in the art would appreciate that simple amino acid removal can be accomplished, and the truncated versions of the sequence simply have to be checked for the desired biological activity in order to determine if such a truncated sequence is still capable of functioning as required. In certain instances, it may be desired to truncate a gene encoding a protein to remove an undesired biological activity, as described herein.

Nucleic acid segments having a desired biological activity may be isolated by the methods described herein. The term "a sequence essentially as set forth in SEQ ID NO:X" means that the sequence substantially corresponds to a portion of SEQ ID NO:X and has relatively few amino acids or codons encoding amino acids which are not identical to, or a biologically functional equivalent of, the amino acids or codons encoding amino acids of SEQ ID NO:X. The term "biologically functional equivalent" is well understood in the art and is further defined in detail herein, as a gene having a sequence essentially as set forth in SEQ ID NO:X, and that is associated with the ability to perform a desired biological activity in vitro or in vivo.

The art is replete with examples of practitioner's ability to make structural changes to a nucleic acid segment (i.e., encoding conserved or semi-conserved amino acid substitutions) and still preserve its enzymatic or functional activity when expressed. See for special example of literature attesting to such: (1) Risler et al. "Amino Acid Substitutions in Structurally Related Proteins. A Pattern Recognition Approach." J. Mol. Biol. 204:1019-1029 (1988) ["... according to the observed exchangeability of amino acid side chains, only four groups could be delineated; (i) Ile and Val; (ii) Leu and Met, (iii) Lys, Arg, and Gln, and (iv) Tyr and Phe."]; (2) Niefind et al. "Amino Acid Similarity Coefficients for Protein Modeling and Sequence Alignment Derived from Main-Chain Folding Anoles." J. Mol. Biol. 219:481-497 (1991) [similarity parameters allow amino acid substitutions to be designed]; and (3) Overington et al. "Environment-Specific Amino Acid Substitution Tables: Tertiary Templates and Prediction of Protein Folds," Protein Science 1:216-226 (1992) ["Analysis of the pattern of observed substitutions as a function of local environment shows that there are distinct patterns . . . Compatible changes can be made."]

These references and countless others, indicate that one of ordinary skill in the art, given a nucleic acid sequence or an amino acid or an amino acid sequence, could make substitutions and changes to the nucleic acid sequence without changing its functionality. One of ordinary skill in the art, given the present specification, would be able to identify, isolate, create, and test DNA sequences and/or enzymes that produce natural or chimeric or hybrid molecules having a desired biological activity. As such, the presently claimed and disclosed invention should not be regarded as being solely limited to the specific sequences disclosed herein. Standardized and accepted functionally equivalent amino acid substitutions are presented in Table I.

TABLE I

| Amino Acid Group | Conservative and Semi-Conservative Substitutions |
| --- | --- |
| Nonpolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

The DNA segments of the present invention encompass DNA segments encoding biologically functional equivalent proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the protein or to test mutants in order to examine biological activity at the molecular level or to produce mutants having changed or novel enzymatic activity and/or substrate specificity.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, such as at least 90 to 95 percent sequence identity, or at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, such as at least 90 percent sequence identity, or at least 95 percent sequence identity, or at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of the Rab5-binding domains and/or the tags utilized in the fusion proteins of the present invention are contemplated as being encompassed by the present invention, providing that the variations in the amino acid sequence maintain at least 75%, such as at least 80%, 90%, 95%, and 99%. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure©. Branden and J. Tooze, eds., Garland Publishing, New York, N.Y. (1991)); and Thornton et al. Nature 354:105 (1991), which are each incorporated herein by reference.

The term "polypeptide" as used herein is a generic term to refer to native protein, fragments, or analogs of a polypeptide sequence. Hence, native protein, fragments, and analogs are species of the polypeptide genus.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "recombinant" in the context of polypeptide coding regions and the polypeptides encoded by such coding regions refers to non-native products wherein the coding regions, and typically the expression thereof, have been manipulated in vitro by man to differ from their occurrence in nature. The polypeptides utilized in the methods of the present invention may be produced in a number of different recombinant systems known in the art, including but not limited to, archeal, prokaryotic, or eukaryotic systems. For expression in an appropriate expression system, the desired viral capsid polypeptide coding regions are operably linked into an expression vector and introduced into a host cell to enable expression. The coding region with the appropriate regulatory regions will be provided in proper orientation and reading frame to allow for expression. Methods for gene construction are known in the art. See, in particular, Molecular Cloning, A Laboratory Manual, Sambrook et al, eds., Cold Spring Harbor Laboratory, Second Edition, Cold Spring Harbor, N.Y. (1989) and the references cited therein.

As used herein, when the term "purified" is used in reference to a molecule, it means that the concentration of the molecule being purified has been increased relative to molecules associated with it in its natural environment. Naturally associated molecules include proteins, nucleic acids, lipids and sugars but generally do not include water, buffers, and reagents added to maintain the integrity or facilitate the purification of the molecule being purified. For example, even if mRNA is diluted with an aqueous solvent during oligo dT column chromatography, mRNA molecules are purified by this chromatography if naturally associated nucleic acids and other biological molecules do not bind to the column and are separated from the subject mRNA molecules.

As used herein, when the term "isolated" is used in reference to a molecule, the term means that the molecule has been removed from its native environment. For example, a polynucleotide or a polypeptide naturally present in a living animal is not "isolated," but the same polynucleotide or polypeptide separated from the coexisting materials of its natural state is "isolated." Further, recombinant DNA molecules contained in a vector are considered isolated for the purposes of the present invention. Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Thus, not all "isolated" molecules need be "purified."

The present invention also includes a purified nucleic acid segment that encodes a fusion protein in accordance with the present invention, further defined as being contained within a recombinant construct or recombinant vector. As used herein, the terms "recombinant vector" and "recombinant construct" refer to a vector/construct that has been modified to contain a nucleic acid segment that encodes a desired protein or fragment thereof. The recombinant vector may be further defined as an expression vector comprising a promoter operatively linked to said nucleic acid segment.

As used herein, the term "vector" refers to an agent (e.g., a plasmid or virus) used to transmit genetic material to a host cell. A vector may be composed of either DNA or RNA. A vector is typically easily manipulated so that one or more encoding segments may be added thereto; in this manner, introduction of the vector into a host cell results in production of a desired protein or peptide encoded by the inserted coding segment under certain growth conditions.

When the terms "one," "a," or "an" are used in this disclosure, they mean "at least one" or "one or more," unless otherwise indicated.

Numerous aspects and advantages of the invention will be apparent to those skilled in the art upon consideration of the following detailed description which provides illumination of the practice of the invention.

The present invention is directed to a fusion protein and methods of using same, as described in detail herein below.

For example, the present invention is also directed to assays for determining intracellular Rab5 activity via levels of Rab5-GTP present in a sample, wherein such methods utilize the fusion protein of the present invention. In one embodiment, such assays are performed utilizing an effector pull-down assay. Such assays provide a fast and efficient method for measuring intracellular Rab5 activity, which is a good indicator for endosome fusion and endocytosis activity of the cell. Such methods overcome the disadvantages and defects of the prior art methods by being easier, faster (can be performed in 2-3 hours), and safer (do not require radioactive reagents).

The fusion protein of the present invention comprises a Rab5-binding domain conjugated to a tag that can bind to an affinity matrix for purification of Rab5-GTP. The Rab5-binding domain specifically binds to the activated form of Rab5.

The term "Rab5-binding domain", as utilized in accordance with the present invention, refers to a peptide or protein that binds specifically to the activated form of Rab5. The Rab5-binding domain may thus contain at least a portion of a Rab5 effector protein; however, it is to be understood that more than just the Rab5-binding domain may be present in the fusion protein, and that the entire Rab5 effector protein may be present in the fusion protein. Examples of Rab5 effector proteins that may be utilized in accordance with the present invention include, but are not limited to, Rabaptin-5, EEA1 (early endosome autoantigen), APPL1 and APPL2 (adaptor protein containing PH domain, PTB domain, and Leucine zipper motif 1 or 2), and Rabenosyn-5. The Rab5-binding domain of the Rab5 effector protein present in the fusion protein may include at least one of the following:

Rabaptin-5 R5BD (residues 739-862):

(SEQ ID NO:1)
ASISSLKAELERIKVEKGQLESTLREKSQQLESLQEIKISLEEQLKKETA
AKATVEQLMFEEKNKAQRLQTELDVSEQVQRDFVKLSQTLQVQLERIRQA
DSLERIRAILNDTKLTDINQLPET;

Rabaptin-5 R5BDs (residues 789-862):

(SEQ ID NO:2)
ATVEQLMFEEKNKAQRLQTELDVSEQVQRDFVKLSQTLQVQLERIRQADS
LERIRAILNDTKLTDINQLPET;

EEA1 R5BD (residues 1-209):

(SEQ ID NO:3)
MLRRILQRTPGRVGSQGSDLDSSATPINTVDVNNESSSEGFICPQCMKSL
GSADELFKHYEAVHDAGNDSGHGGESNLALKRDDVTLLRQEVQDLQASLK
EEKWYSEELKKELEKYQGLQQQEAKPDGLVTDSSAELQSLEQQLEEAQTE

-continued
NFNIKQMKDLFEQKAAQLATEIADIKSKYDEERSLREAAEQKVTRLTEEL
NKEATVIQD.

It is to be understood that the fusion protein may include additional sequences attached to the Rab5-binding domains disclosed herein above. For example, the fusion protein may contain an entire Rab5 effector protein rather than simply the Rab5-binding domain of such effector protein. Therefore, it is to be understood that the present invention is not limited to the specific sequences disclosed above, but rather includes any portion of a Rab5 effector molecule (or entire Rab5 effector molecule) capable of specifically binding to the activated form of Rab5.

In addition, the Rab5-binding domain of the fusion protein may be a mutant or derivative of any of the sequences above, or of any Rab5-binding domain known in the art, so long as the mutant or derivative maintains the ability to specifically bind Rab5-GTP. For example, the Rab5-binding domain may be a sequence having less than 10 amino acid substitutions when compared to at least one of SEQ ID NOS:1-3; a sequence having less than 5 amino acid substitutions when compared to at least one of SEQ ID NOS:1-3; or a sequence having less than 3 amino acid substitutions when compared to at least one of SEQ ID NOS:1-3. Alternatively, the Rab5-binding domain may be a sequence having at least 80% sequence identity when compared to at least one of SEQ ID NOS:1-3; a sequence having at least 85% sequence identity when compared to at least one of SEQ ID NOS:1-3; or a sequence having at least 90% sequence identity when compared to at least one of SEQ ID NOS:1-3.

The tag present in the fusion protein may be any tag known in the art that can bind to form an affinity matrix for purification of Rab5-GTP. Examples of tags that may be utilized in accordance with the present invention include, but are not limited to, the following:

The glutathione S-transferase (GST) epitope, which binds to glutathione:

(SEQ ID NO:4)
MSPILGYWKIKGLVQPTRLLLEYLEEKYEEHLYERDEGDKWRNKKFELGL
EFPNLPYYIDGDVKLTQSMAIIRYIADKHNMLGGCPKERAEISMLEGAVL
DIRYGVSRIAYSKDFETLKVDFLSKLPEMLKMFEDRLCHKTYLNGDHVTH
PDFMLYDALDWLYMDPMCLDAFPKLVCFKKRIEAIPQIDKYLKSSKYIAW
PLQGWQATFGGGDHPPKSDLIEGRGIPGNS;

The 6-His epitope, which binds to a metal column (such as but not limited to, nickel or zinc):

HHHHHH;             (SEQ ID NO:5)

The Maltose Binding Protein, which binds to an amylase column:

(SEQ ID NO:6)
MKIEEGKLVIWINGDKGYNGLAEVGKKFEKDTGIKVTVEHPDKLEEKFPQ
VAATGDGPDIIFWAHDRFGGYAQSGLLAEITPDKAFQDKLYPFTWDAVRY
NGKLIAYPIAVEALSLIYNKDLLPNPPKTWEEIPALDKELKAKGKSALMF
NLQEPYFTWPLIAADGGYAFKYENGKYDIKDVGVDNAGAKAGLTFLVDLI
KNKHMNADTDYSIAEAAFNKGETAMTINGPWAWSNIDTSKVNYGVTVLPT
FKGQPSKPFVGVLSAGINAASPNKELAKEFLENYLLTDEGLEAVNKDKPL
GAVALKSYEEELAKDPRIAATMENAQKGEIMPNIPQMSAFWYAVRTAVIN
AASGRQTVDEALKDAQTN.

It is to be understood that the tag present in the fusion protein may include additional sequences in addition to those disclosed herein above. In addition, it is to be understood that the present invention is not limited to the specific sequences disclosed above, but rather includes any mutants or variations of SEQ ID NOS:4-6 which maintain the ability to function as a tag utilized for affinity purification. Further, the present invention includes the use of any tag known in the art. The use of tags as portions of fusion proteins for affinity purification is well known in the art, and therefore no further discussion regarding tags is deemed necessary for practice of the present invention.

The fusion protein may be produced by any recombinant method known in the art, utilizing known vectors for production of fusion proteins containing tags. Such vectors include, but are not limited to, pGEX vectors and pMAL vectors. Gene fusion vectors are commercially available and well known in the art, and therefore no further discussion regarding the use thereof in accordance with the present invention is deemed necessary.

Once the fusion protein is produced, it is contacted with a matrix or resin containing a molecule to which the tag specifically binds, thereby forming an affinity matrix. Examples of affinity molecules to which the tag binds are known in the art, and it is within the skill of a person of ordinary skill in the art to select an appropriate affinity molecule based on the tag present in the fusion protein. Examples of specific affinity molecules that may be utilized include, but are not limited to, glutathione, which binds to GST; nickel or zinc, which binds to the 6-His tag; and amylase, which binds to MBP. However, it is to be understood that these examples are not limiting, and any affinity molecules known in the art as capable of binding to a tag utilized in the fusion protein may be utilized. The resin may be any molecule capable of immobilizing the affinity molecule, such as but not limited to, agarose beads, such as but not limited to, SEPHAROSE™. Examples of other resins are commercially available and well known in the art, and therefore no further discussion thereof is deemed necessary.

Once the affinity matrix is produced, a cell lysate may be contacted with the affinity matrix such that Rab5-GTP present in the cell lysate will specifically bind to the affinity matrix, thus forming a mixture. The AMOUNT OF Rab5-GTP present in the mixture is then determined. For example, the mixture may then be rinsed to remove the cell lysate, and then subjected to gel electrophoresis followed by immunoblot analysis (such as with an anti-Rab5 antibody). As a control, an aliquot of the total cell lysate may be utilized to provide an amount of total Rab5, that is, both Rab5-GTP (active form) and Rab5-GDP (inactive form), present in the sample.

In an alternative embodiment, the affinity matrix may be immobilized on a solid support, such as a column utilized in affinity chromatography. The cell lysate is run through the column to allow binding of Rab5-GTP present in the cell lysate to the affinity column, and a wash buffer is then run through the column to remove the cell lysate. An elution buffer is then applied to the column and collected, whereby the Rab5-GTP attached to the column is eluted therefrom and present in the collected elution buffer. Elution buffers utilized with affinity chromatography using tags such as 6-His, GST and MBP are commercially available and widely known in the art, and therefore no further discussion thereof is deemed necessary. The amount of Rab5-GTP present in the collected elution buffer is then determined, such as but not limited to, by subjecting the collected elution buffer to gel electrophoresis followed by immunoblot analysis as described above. As a control, an aliquot of the total cell lysate may be utilized to provide an amount of total Rab5, that is, both Rab5-GTP (active form) and Rab5-GDP (inactive form), present in the sample.

The present invention is also directed to a recombinant construct that comprises a recombinant vector (as described herein above) and a nucleic acid segment encoding the fusion protein described in detail herein above.

The present invention is also directed to kits that may be utilized in accordance with the present invention, such as but not limited to, to determine intracellular levels of Rab5-GTP present in a sample.

In one embodiment, the kit comprises the recombinant construct described herein above, either alone or in combination with one or more components, such as but not limited to, a quantity of the affinity matrix to which the tag of the fusion protein binds; one or more buffers (i.e., cell lysis buffer, rinse buffer, elution buffer, pull down assay buffer, etc.); anti-Rab5 antibody, and the like.

In another embodiment, the kit may comprise a conjugate that includes the fusion protein described herein above conjugated to the affinity matrix. This embodiment of the kit may also include one or more components such as but not limited to, one or more buffers (i.e., cell lysis buffer, rinse buffer, elution buffer, pull down assay buffer, etc.); anti-Rab5 antibody, and the like.

Examples are provided hereinbelow. However, the present invention is to be understood to not be limited in its application to the specific experimentation, results and laboratory procedures. Rather, the Examples are simply provided as one of various embodiments and are meant to be exemplary, not exhaustive.

EXAMPLE 1

Nerve growth factor (NGF) is a neurotrophin that is essential for survival and differentiation of neuronal cells (Huang and Reichardt, 2001; Segal, 2003). Endocytosis and intracellular trafficking of NGF-TrkA (a high-affinity NGF receptor) complex is necessary for a successful NGF signal transduction process to induce neurite outgrowth (Grimes et al., 1996; Zhang et al., 2000), a hallmark of neuron differentiation, in PC12 cells (a rat pheochromocytoma cell line) (Greene and Tischler, 1976). However, molecular components of the endocytic machinery involved are yet to be identified and characterized.

Rab5 is a small GTPase localized on early endosomes, and it controls early endosome fusion along the endocytic pathway (Gorvel et al., 1991; Bucci et al., 1992; Li and Stahl, 1993; Rybin et al., 1996; Li and Liang, 2001). A population of Rab5-positive early endosomes also contains endocytosed NGF-TrkA complexes, and these endosomes are called signaling endosomes (Delcroix et al., 2003). It is suggested that the endocytosed and activated TrkA may recruit proteins to activate the small GTPase Rap1 on the signaling endosomes (York et al., 2000; Zhang et al., 2000). One such pathway may involve the FRS-2/Crk/C3G adaptor system (Meakin et al., 1999; Nosaka et al., 1999). Activated Rap1 in turn activates B-Raf, leading to prolonged activation of extracellular signal-regulated kinases (York et al., 1998), which is associated with neurite outgrowth and cell differentiation. Furthermore, blocking the endocytosis of NGF-TrkA with a dynamin mutant is known to inhibit NGF-induced neurite outgrowth in PC12 cells (Zhang et al., 2000). Thus, NGF signaling on signaling endosomes is thought to be important for neurite outgrowth and differentiation.

An important question to be resolved is the nature and biogenesis of the signaling endosomes. Although signaling endosomes contain early endosomal markers such as Rab5, they are long-lived, and they are suggested to undergo long-distance retrograde transport from the axon to the cell body of neurons (Howe and Mobley, 2004). Their relationship with conventional early endosomes is unclear, although it is possible that they are specialized early endosomes that are temporarily diverted from the conventional endocytic/degradation pathway to sustain the NGF signaling. In this regard, Rab5 controls the entry to early endosomes and endocytic pathway (Ceresa and Schmid, 2000; Rink et al., 2005). Thus, the present invention is directed to an investigation into the activity and function of Rab5 in NGF-mediated neurite outgrowth in PC12 cells.

Materials and Methods

Plasmids and cDNAs: pBI and pBI/EGFP were purchased from BD Biosciences (San Jose, Calif.). The cDNAs of Rab5: wild type (WT), Rab5:Q79L, Rab5:S34N, and Rab5:N133I were generated by polymerase chain reaction (PCR) with the previously made pGEX or pH2J1 constructs as templates (Liang et al., 2000; Li and Liang, 2001) and subcloned into the MluI restriction site of pBI and pBI/EGFP. Rat RabGAP5 cDNA was purchased from Invitrogen (Carlsbad, Calif.). The TrkA, RN-tre, and TSC2 cDNAs were kindly provided by Brian Rudkin (Laboratoire de Biologie Moleculaire et Cellulaire, Lyon, France), P. Paolo Di Fiore (European Institute of Oncology, Milan, Italy), and Kun-Liang Guan (Department of Biological Chemistry, University of Michigan, Ann Arbor, Mich.), respectively. The TrkA cDNA was subcloned into the MluI site of pBI. The RabGAP5 and RN-tre cDNAs were subcloned in pcDNA3 and pBI/TrkA vectors, either with or without the Myc tag.

Antibodies: The affinity-purified rabbit anti-RabGAP5 antibody was kindly provided by Francis Barr's laboratory (Max-Planck Institute of Biochemistry, Martinsried, Germany). Monoclonal antibodies for actin, FLAG, and Myc were purchased from Sigma-Aldrich (St. Louis, Mo.), whereas the anti-Rab5 monoclonal antibody (mAb), anti-hemagglutinin (HA) mAb, and anti-TrkA rabbit antiserum were from BD Biosciences, Santa Cruz Biotechnology (Santa Cruz, Calif.), and Upstate Biotechnology (Lake Placid, N.Y.), respectively. The anti-pTrkA rabbit antiserum was from Cell Signaling Technology (Beverly, Mass.).

Cell Culture and Transfection: Tet-Off PC12 cells (BD Biosciences) were grown in 35-mm culture dishes in DMEM (Invitrogen) supplemented with 10% heat-inactivated horse serum (Invitrogen), 5% heat-inactivated fetal bovine serum (FBS; Invitrogen), 20 U/ml penicillin/streptomycin (Invitrogen), 1 mM I-glutamine (Invitrogen), and 200 µg/ml Geneticin (G-418; Invitrogen). Cells were incubated at 37° C. in a humidified incubator with 10% $CO_2$. For transfection, cells were seeded at a density of $2\times10^5$ cells/dish, grown to 70-80% confluence, and transfected with the indicated plasmids by using Lipofectamine 2000 (Invitrogen) according to the manufacturer's protocol.

Neurite Outgrowth Assay: After cotransfection with pBI/EGFP, cells were allowed to recover in full growth medium and to express the recombinant proteins for 24 h. The growth medium was then replaced with a medium containing only 0.5% horse serum (no FBS) and 50 ng/ml NGF. The medium was incubated at 37° C. for 6 d, with replenishment of NGF every 2 d until the sixth day. The NGF concentration was 50 ng/ml unless indicated otherwise. On different days as indicated, cells were fixed in 4% paraformaldehyde (Electron Microscopy Sciences, Hatfield, Pa.) for 30 min, and neurite outgrowth was observed with either an inverted fluorescence microscope (transiently transfected cells) or a phase-contrast microscope (cloned cell lines). A Nikon Diaphot 300 microscope was used for both purposes. The images were captured by a digital camera, stored in a connected computer, and analyzed with the Nikon ACT-1 software. Differentiated cells were defined as those containing at least one neurite twice as long as the cell body diameter. The percentage of differentiated cells in each case was determined from transfected cells (i.e., cells expressing green fluorescent protein). Standard error of the mean (SEM) was calculated from three to five independent experiments.

Confocal Fluorescence Microscopy: A Leica confocal laser scanning microscope with Ar-488 and Kr-568 laser excitation in the Flow and Image laboratory on campus was used, and a procedure described previously (Li and Liang, 2001) was followed. Briefly Tet-Off PC12 cells were grown on coverslips coated with collagen IV and transfected with pBI and/or pcDNA3 constructs expressing various enhanced green fluorescent protein (EGFP)-Rab5:S34N, EGFP-Rab5:Q79L, red fluorescent protein (RFP)-Rab5:Q79L, TrkA, or TrkA-EGFP as indicated. RFP represents ds-Red monomer from BD Biosciences. At 24 h posttransfection, the cells were treated with 50 ng/ml NGF for the indicated times, and then they were processed for immunofluorescence microscopy. Cells were rinsed three times with phosphate-buffered saline (PBS) and fixed for 20 min with 4% paraformaldehyde (wt/vol in PBS) at room temperature, followed by permeabilization with 0.1% Triton X-100 (in PBS) for 5 min. The cells were then stained with the antipTrkA antibody that specifically recognizes the cytoplasmic domain of activated TrkA and a secondary antibody (goat anti-rabbit IgG conjugated with Alexa568; Invitrogen). The coverslips were then mounted in PBS on glass slides and viewed with the Leica confocal microscope.

Glutathione S-Transferase (GST) Pull-Down Assay: The cDNA of the Rab5-binding domain (R5BD, residues 739-862) of Rabaptin5 was cloned into the pGEX vector (GE Healthcare, Little Chalfont, Buckinghamshire, United Kingdom). The resulting construct was termed pGEX/Rabaptin-5 (R5BD), which expressed the fusion protein GST-R5BD in the *Escherichia coli* strain DH5α upon isopropyl β-D-thiogalactoside induction. GST-R5BD was then affinity purified with glutathione-Sepharose 4B resin (GE Healthcare). Rab5 proteins (WT, Q79L, and S34N) were expressed in Tet-Off PC12 cells by transfection of corresponding pBI constructs and incubation at 37° C. for 24 h. Cells were then treated with 50 ng/ml NGF for the indicated times (untreated cells served as controls), followed by washing with ice-cold PBS and lysis for 5 min in the lysis buffer, which contained 25 mM HEPES, pH 7.4, 100 mM NaCl, 5 mM $MgCl_2$, 0.1% NP-40, 10% glycerol, 1 mM dithiothreitol, and protease inhibitor cocktail (Sigma-Aldrich). Lysates were clarified by centrifugation at 10,000 g for 2 min at 4° C., and an aliquot (200 µl) of the supernatant was incubated with 20 µl of GST-R5BD bound to the glutathione-Sepharose4B resin for 10 min at 4° C. on a rotating mixer. The resin was subsequently rinsed with the lysis buffer, resuspended in SDS sample buffer, boiled for 3 min, and subjected to SDS-PAGE (15% gel), followed by immunoblot analysis with the anti-Rab5 mAb. The results were quantified by densitometry using Densitometer SI (GE Healthcare).

In vivo GTPase-activating Protein (GAP) Assay: Cells were cotransfected with pBI/Rab5 and a pBI or pcDNA3 construct expressing one of the GAPs. At 24 h posttransfection, the Rab5-GTP level in the cell was determined by the GST pull-down assay described above.

Establishment of Stable PC12 Cell Lines: Tet-Off PC12 cells were cotransfected with pBI/FLAG-Rab5:Q79L (or pBI/FLAG-Rab5:S34N) and pTK-hyg at a 20:1 ratio by using the Lipofectamine 2000-mediated procedure as described above. The cells were then selected with 150 µg/ml hygromycin (BD Biosciences) in the presence of 1 µg/ml doxycycline (Dox; BD Biosciences). After 3 wk, hygromycin-resistant colonies began to grow. Individual colonies were isolated and transferred to 24-well plates in triplicates, with two samples maintained in the presence of Dox and one sample without Dox to induce the expression of cloned Rab5 proteins for 2 d. Recombinant Rab5 proteins containing the FLAG epitope were identified by immunoblot analysis with the anti-FLAG antibody, and clones with inducible recombinant protein expression were selected and scaled up for further assays.

Cell Growth Rate: Cells were seeded at a density of $1 \times 10^5$ cells/well in a six-well plate and incubated at 37° C. Cell numbers were counted each day up to 6 d with a hemacytometer (Hausser Scientific, Horsham, Pa.), after trypsinization and resuspension in the medium at each time point. The results were averaged from triplicate samples, and error bars represented SEM from three independent experiments.

Coimmunoprecipitation (coIP) Assay: Cells were transfected with pBI/TrkA constructs that coexpressed RabGAP5 or mutants (all contained Myc tag) via Lipofectamine 2000 as described above. Cells were allowed to recover in full growth medium and to express the recombinant proteins for 24 h at 37° C. Before cell lysis, cells were starved in serum-free medium for 24 h and then either treated or not treated with 50 ng/ml NGF for 5 min as indicated. Cells were then rinsed with ice-cold PBS, pH 7.4, and lysed on ice for 45 min in the lysis buffer, which contained 20 mM Tris-HCl, pH 7.4, 150 mM NaCl, 1% Triton X-100, 2 mM sodium orthovanadate, 2 mM para-nitrophenol phosphate, and protease inhibitor cocktail (Sigma-Aldrich). After clearing at 10,000×g for 15 min, cell lysates were incubated with anti-Myc antibody-conjugated agarose beads (Sigma-Aldrich) for 4 h at 4° C. The beads were then washed four times with the lysis buffer and boiled for 3 min in SDS sample buffer, followed by SDS-polyacrylamide gel electrophoresis (PAGE) and immunoblot analysis with anti-TrkA, anti-pTrkA, and anti-Myc antibodies. The results were quantified by densitometry using Densitometer SI (GE Healthcare).

RNA Interference (RNAi) of RabGAP5 : The pSUPER vector (Oligoengine) was used to express specific short hairpin RNAs (shRNAs) to knock down RabGAP5 expression in PC12 cells. The 19- or 21-mer oligonucleotides were designed, annealed, and then cloned into pSUPER according to the manufacturer's instructions. The targeting regions included four sequences in rat RabGAP5 and one sequence in its human counterpart as a control, including 5'-GCATCTGGGACCTGTTCTTCT-3' (for rat shRNA1; SEQ ID NO:7), 5'-GCCCTATTTGAACATGGATTG-3' (for rat shRNA2; SEQ ID NO:8), 5'-GGCAAAGAACATCAAA-CAA-3' (for rat shRNA3; SEQ ID NO:9), 5'-GGC-CCTATTTGMCATGGA-3' (for rat shRNA4; SEQ ID NO:10), and 5'-GCAGAGCAACCAGAGTTCTAC-3' (for human shRNA; SEQ ID NO:11).

The effectiveness of RabGAP5 knockdown was confirmed by immunoblot analysis. Because of low transfection efficiency, the shRNA constructs were cotransfected with pBI/myc-RabGAP5, followed by immunoblot analysis 48 h later with the anti-myc mAb to examine the level of myc-RabGAP5 expression. For neurite outgrowth analysis, PC12 cells were transfected with either the pSUPER vector alone as a negative control or with each of the shRNA constructs. In this case, pBI/EGFP was cotransfected to identify the transfected cells by fluorescence microscopy, and neurite outgrowth was measured at 48 h posttransfection and for 5 days thereafter with the assay described above.

Results

Transient Expression of Rab5 and a Constitutively Active Mutant (Rab5:Q79L) Blocks NGF-mediated Neurite Outgrowth. Constitutively active as well as dominant-negative mutants of Rab5 were used in this study. Rab5:Q79L is a constitutively active mutant, because it is defective in GTP hydrolysis and it is locked in the active GTP-bound conformation (Li and Stahl, 1993; Stenmark et al., 1994; Li and Liang, 2001). Rab5:S34N and Rab5:N133I are dominant-negative mutants, because they are defective in GTP binding and they are either nucleotide free or guanosine diphosphate (GDP) bound (Li and Stahl, 1993; Li et al., 1994; Stenmark et al., 1994; Hoffenberg et al., 1995). Their dominant-negative phenotype is thought to be due to sequestration of Rab5 guanine-nucleotide exchange factor (GEF)(s), which is normally required for activating the endogenous Rab5 via stimulating GDP dissociation. WT Rab5 and each of the mutants were expressed in a Tet-Off PC12 cell line by using the bidirectional expression vector pBI/EGFP, which expressed EGFP and each cloned Rab5 protein simultaneously. Protein expression in this system was controlled by Dox (a stable analogue of tetracycline). On removal of Dox from the medium, the cloned WT and mutant Rab5 proteins were induced to show robust expression as confirmed by immunoblot analysis (FIG. 1A).

The effect of overexpressing WT and mutant Rab5 proteins on NGF-mediated neurite outgrowth was next determined. Tet-Off PC12 cells were transfected with either the pBI/EGFP vector itself or the various pBI/EGFP constructs expressing WT or mutant Rab5 proteins, in the absence of Dox to promote expression. NGF was added the next day to induce neurite outgrowth, and cells expressing EGFP were identified by fluorescence microscopy. EGFP expression here served as a marker for transfected cells, which should also express the indicated Rab5 protein from the same vector. After 6 d of NGF treatment, the neurite length in the EGFP-expressing cells was measured, and the percentage of differentiated cells was determined. In control cells transfected with the pBI/EGFP vector, 60% of them differentiated into sympathetic neuron-like phenotype with long neurites (FIG. 1, B and C). Overexpression of either dominant-negative mutant (Rab5:S34N or Rab5:N133I) did not significantly affect the neurite outgrowth under this condition (i.e., 50 ng/ml NGF) (FIG. 1, B and C). In contrast, overexpression of WT or the constitutively active Rab5:Q79L mutant dramatically inhibited neurite outgrowth, with <10% of the cells containing extended neurites (FIG. 1, B and C). When NGF concentration was reduced to 10 ng/ml, cells expressing either dominant-negative mutant (Rab5:S34N or Rab5:N133I) remained able to grow neurites, whereas control PC12 cells failed to do so (data not shown). Together, these results suggest that high Rab5 activity is unfavorable to neurite outgrowth and that endogenous Rab5 function may need to be suppressed during NGF-induced neurite outgrowth and cell differentiation.

Figure 2:
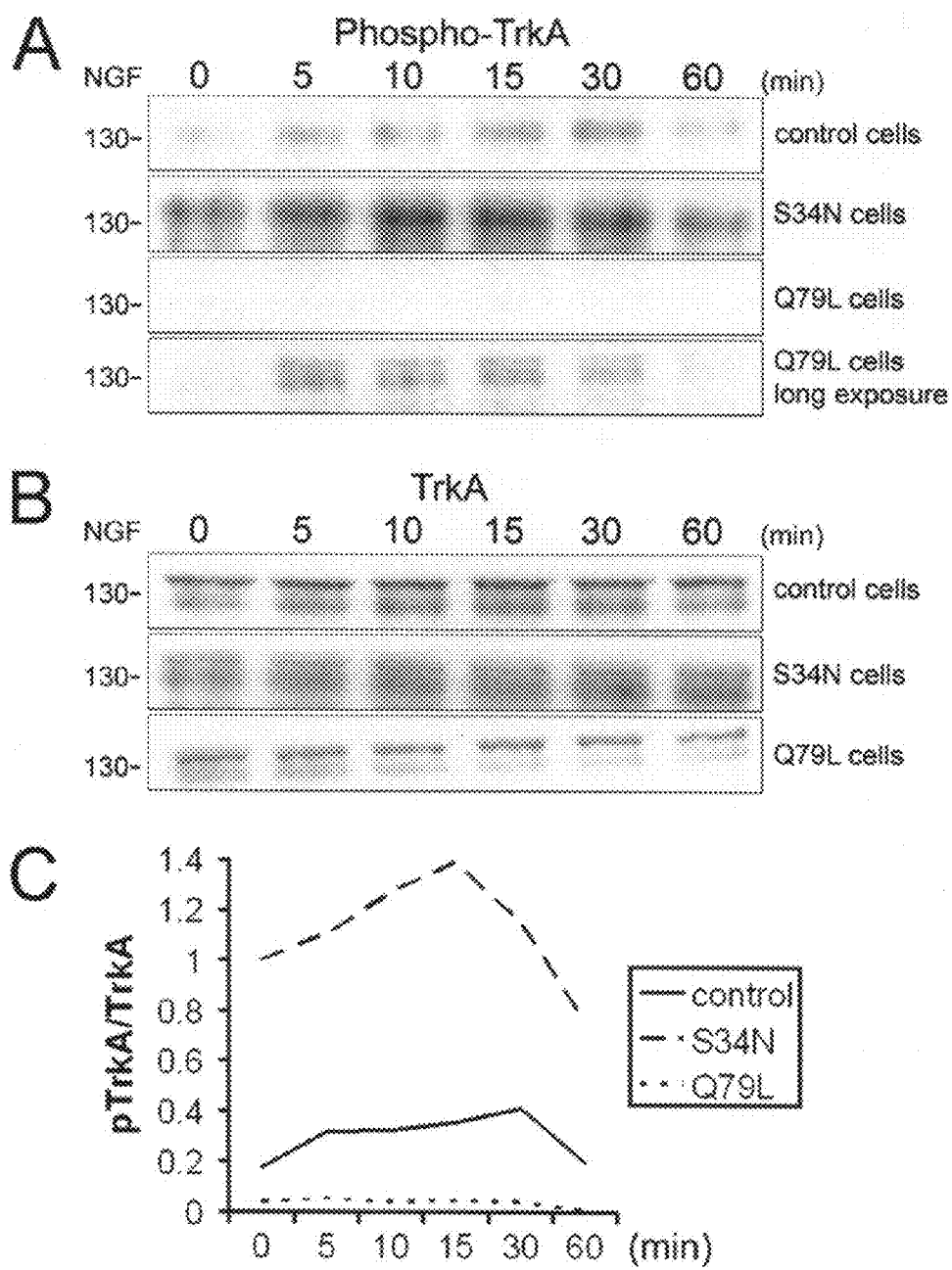
FIG. 2 illustrates the effect of Rab5 mutants on TrkA activation. (A) Immunoblot analysis of activated TrkA with the anti-pTrkA antibody. PC12 cells coexpressing TrkA and the indicated Rab5 mutants (Rab5:S34N or Rab5:Q79L) were treated with 50 ng/ml NGF for the indicated times, followed by cell lysis and immunoblot analysis with the anti-pTrkA antibody. Control cells expressed TrkA only. The signal for Rab5:Q79L samples is low and can be detected only after longer exposure (10 times) of the blot as indicated. Molecular mass standards (in kilodaltons) are indicated on the left of each panel. (B) Immunoblot analysis of total TrkA with the anti-TrkA antibody on the same membranes after stripping off the previous anti-pTrkA antibody. (C) Relative amounts of pTrkA versus total TrkA in each sample determined by densitometry of the blots in A and B. Because of different antibodies used, the ratio does not reflect absolute percentage of pTrkA, but it serves the purpose to compare the relative levels of pTrkA in control, Rab5:S34N, and Rab5:Q79L cells.

Inactivation of Rab5 Facilitates Intracellular NGF Signaling. The effect of expressing Rab5:S34N and Rab5:Q79L on NGF signaling was further investigated directly by determining the phosphorylation profile of TrkA upon NGF treatment. In this case, TrkA was coexpressed with either Rab5:S34N or Rab5:Q79L to enhance the ratio of relevant TrkA detection signal in transfected cells versus TrkA background in untransfected cells. Cells were treated with NGF for different times, followed by immunoblot analysis of cell lysates with anti-phospho-TrkA (pTrkA) and anti-TrkA antibodies (FIG. 2). The former antibody recognizes the activated, $Tyr^{490}$-phosphorylated form only. A striking observation was that TrkA phosphorylation/activation was dramatically decreased in Rab5:Q79L-expressing cells, whereas the activation signal was enhanced in Rab5:S34N-expressing cells and sustained for a longer period, in comparison with control cells that expressed TrkA only (FIG. 2A). There was a steady-state, basal level of pTrkA, which increased upon NGF treatment. The pTrkA level in Rab5:Q79L-expressing cells was always lower than that in control and Rab5:S34Nexpressing cells before and after NGF treatment (FIG. 2A).

Even the NGF-enhanced pTrkA level in Rab5:Q79L-expressing cells was much lower than that of the basal pTrkA level in Rab5:S34N-expressing cells (FIG. 2A), Indeed, there was much higher percentage of pTrkA among total TrkA in Rab5:S34N-expressing cells than in Rab5:Q79L-expressing cells (FIGS. 2, B and C). Because the total TrkA level in control, Rab5:S34N-expressing, and Rab5:Q79L-expressing cells was similar (FIG. 2B), the low pTrkA level seen in Rab5:Q79L-expressing cells was most likely due to rapid dephosphorylation in Rab5:Q79L endosomes rather than to receptor degradation.

Figure 3:
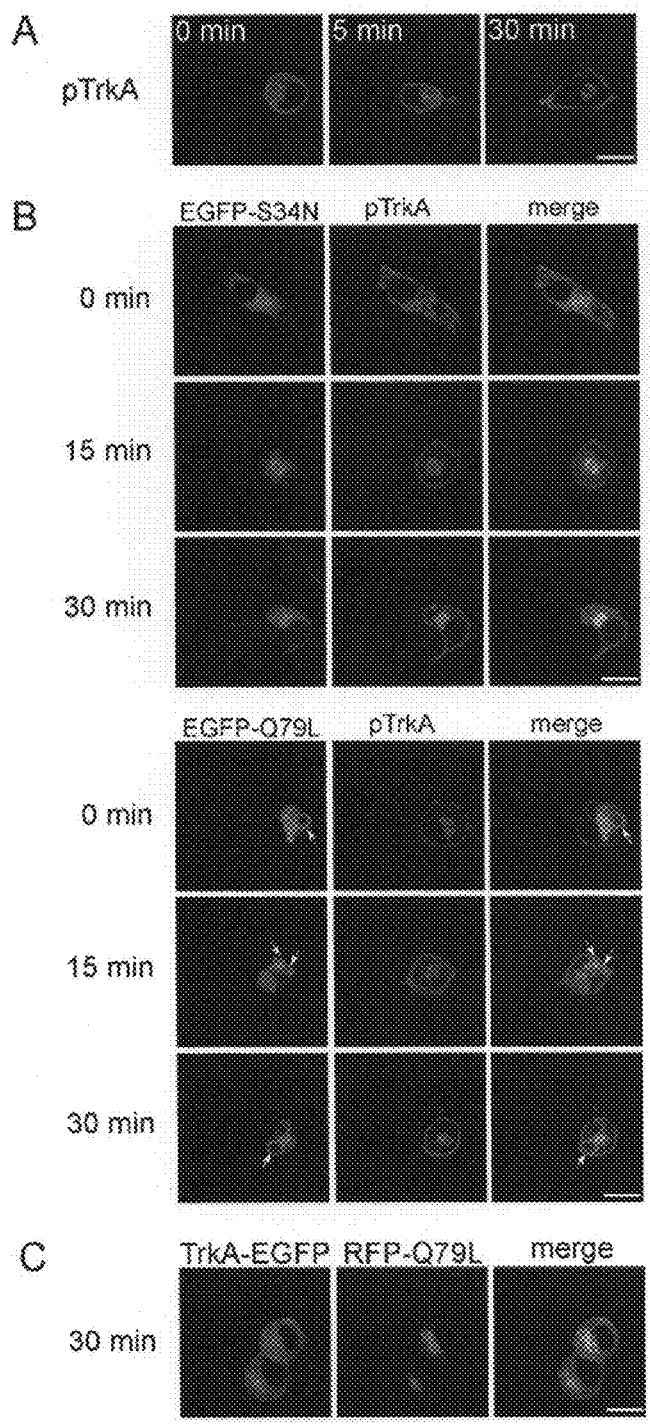
FIG. 3 illustrates accumulation of activated pTrkA on endosomes where Rab5 activity is blocked. (A) Confocal microscopic images showing the localization of pTrkA in control PC12 cells transfected with pBI/TrkA upon 0-, 5-, and 30-min NGF treatment as indicated. The cells were stained by the anti-pTrkA antibody and goat anti-rabbit IgG conjugated with Alexa568. Bar, 16 μm. (B) Confocal microscopic images showing the localization of EGFP-Rab5:S34N and pTrkA or EGFP-Rab5:Q79L and pTrkA in PC12 cells cotransfected with pBI/EGFP-Rab5:S34N and pBI/TrkA or pBI/EGFP-Rab5:Q79L and pBI/TrkA upon 0-, 15-, and 30-min NGF treatment as indicated. Arrows indicate the large Rab5:Q79L vesicles devoid of pTrkA. Bar, 16 μm. (C) Confocal microscopic images showing the localization of TrkAEGFP and RFP-Rab5:Q79L in PC12 cells transfected with TrkAEGFP and pBI/RFP-Rab5:Q79L upon 30-min NGF treatment as indicated. Bar, 16 μm.
Figure 6:
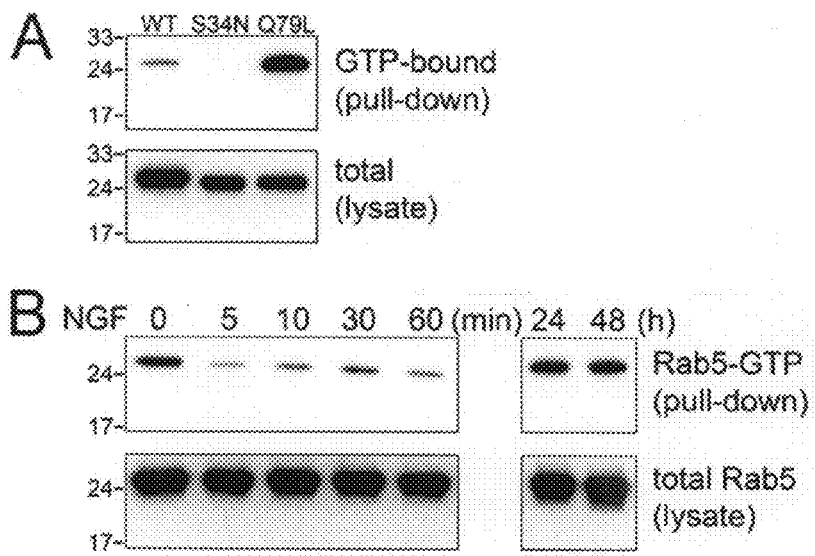
FIG. 6 illustrates NGF-induced reduction of Rab5-GTP level in PC12 cells. (A) PC12 cells were transfected with plasmids that express Rab5:WT, Rab5:S34N, and Rab5:Q79L as indicated. Cells were then lysed, and cell lysates were incubated with GST-R5BD. GTP-bound Rab5 fraction bound to GST-R5BD (pull-down) and total amount of Rab5 proteins in the lysates (cell lysate, the amount loaded was 5% that used for the pull-down) were detected by immunoblot analysis with the anti-Rab5 antibody. (B) The cells that overexpressed Rab5:WT were treated with 50 ng/ml NGF for the indicated times, followed by cell lysis and pull-down assays as described in A. Control cells (control) were not treated with NGF.

To test the aforementioned contention, confocal fluorescence microscopy was performed to determine whether pTrkA would accumulate or diminish in Rab5:S34N- or Rab5:Q79L containing endosomes. In control PC12 cells transfected with TrkA alone, activated pTrkA was detected at plasma membrane as well as dispersed intracellular structures at steady state (FIG. 3A). NGF induced endocytosis and accumulation of pTrkA near the nucleus, presumably on signaling endosomes (FIG. 3A). There seemed to be an immobile fraction of pTrkA that remained on the plasma membrane and that was not internalized into endosomes (FIG. 3A, 30 min), even after 1-h NGF treatment (data not shown). The plasma membrane-localized pTrkA may not be relevant to neurite growth, because endocytosis and signaling on endosomes is required for neurite outgrowth (Zhang et al., 2000). The focus was on the internalized pool of pTrkA. In Rab5:S34N-expressing cells, endocytosed pTrkA colocalized to Rab5:S34N-containing endosomes and increasingly concentrated at the perinuclear region upon NGF treatment (FIG. 3B). In contrast, there was no strong accumulation of pTrkA at the perinuclear region in Rab5:Q79L-expressing cells with or without NGF treatment (FIG. 3B). The Rab5:Q79L-containing endosomes are more heterogeneous in size depending on the number of fusion events, and there are small/young endosomes as well as large/mature endosomes. Importantly intracellular pTrkA showed no colocalization with Rab5:Q79L on the large/mature endosomes and only partially localized to the small/young endosomes (FIG. 3B), even though total TrkA (in the form of TrkA-EGFP) colocalized well with Rab5:Q79L on both types of endosomes (FIG. 3C). TrkA-EGFP was previously shown to follow the same endocytic pathway as TrkA (Jullien et al., 2002). The data provide further evidence that the activation status of pTrkA is more transient in Rab5:Q79L endosomes that contain high Rab5 activity for endosome fusion than in Rab5:S34N endosomes where Rab5 activity and endosome fusion is blocked. The pTrkA is progressively inactivated by dephosphorylation as it enters Rab5:Q79L endosomes, probably by gaining access to the endosome-associated phosphatases. Along this line, pTrkA in Rab5:S34N endosomes avoids dephosphorylation and inactivation leading to sustained signaling and higher steady level of pTrkA, because it cannot get access to the phosphatases due to a block of Rab5 activity and early endosome fusion. Thus, enhanced TrkA signaling in cells expressing Rab5:S34N and compromised signaling in cells expressing Rab5:Q79L are consistent with the effects of these mutants on neurite outgrowth (FIG. 1). Like Rab5:S34N, NGF also down-regulates Rab5 activity, via RabGAP5, in PC12 cells to facilitate neurite outgrowth (FIG. 6; see below).

The defective NGF signaling and neurite outgrowth seen in cells overexpressing WT or Rab5:Q79L was not due to any negative effect on cell growth. This point was confirmed by the following experiments in which cell lines expressing Rab5:Q79L and Rab5:S34N, respectively, were established.

Figure 4:
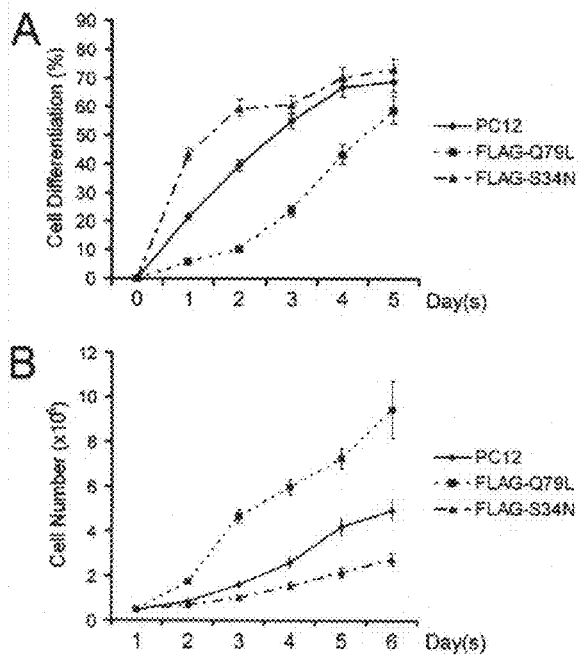
FIG. 4 illustrates neurite outgrowth and cell growth rate of cloned PC12 cell lines expressing FLAG-Rab5:Q79L and FLAG-Rab5:S34N. (A) Comparison of neurite outgrowth in the parental (PC12) cell line and the cell lines expressing FLAG-Rab5:S34N and FLAG-Rab5:Q79L as indicated, in the absence of Dox to induce protein expression. On addition of 50 ng/ml NGF, neurite outgrowth was quantified each day as described in the legend to FIG. 1. (B) Comparison of cell growth rates in the PC12 cell line and the cell lines expressing FLAG-Rab5:S34N and FLAG-Rab5:Q79L as indicated. Each cell line was seeded at $10^5$ cells/35-mm dish and grown in the absence of Dox. Each day thereafter, cells were trypsinized, and the cell number was determined by using a hemacytometer. Error bars represent SEM of three independent experiments.

Cloned PC12 Cell Lines: Rab5:Q79L Expression Inhibits, but Rab5:S34N Expression Promotes, NGF-mediated Neurite Outgrowth. To extend the transient expression results, a number of Tet-Off PC12 cell lines were established that expressed the Rab5 mutants upon Dox removal (Supplemental FIG. 1). Consistent with the transient expression data (FIG. 1), expression of Rab5:Q79L inhibited NGF-induced neurite outgrowth, whereas expression of Rab5:S34N facilitated neurite outgrowth (FIG. 4A). In this case, neurite outgrowth was observed and quantified each day upon NGF treatment. Rab5:Q79L-expressing cell lines showed slower neurite outgrowth. The extent of inhibition was less than the transient expression results, possibly due to the lower expression level and/or adjustment and adaptation of the cells. Rab5:S34N facilitated neurite outgrowth in the sense that these cells were more sensitive to NGF treatment. Although it usually took 5 d for the control parental cells to reach maximal neurite outgrowth, it only took 2-3 d for the Rab5:S34N-expressing cells to reach a similar level (FIG. 4A). Although the results in FIG. 4A were obtained from clone 1 of FLAG-Rab5:Q79L cell lines and clone 1 of FLAG-Rab5:S34N cell lines (Supplemental FIG. 1), clone 2 of both cell lines were examined, and the same results were obtained. Furthermore, growth rates of the Rab5:Q79L- and Rab5:S34N-expresssing cell lines were determined over a 6-d period, and it was found that the Q79L-expressing cells grew faster and the S34N-expressing cells grew slower than the control parental PC12 cells (FIG. 4B). Again, both cell clones for each mutant showed similar results. In PC12 cells, NGFinduced neurite outgrowth and cell differentiation is usually accompanied by decreased cell growth rate (Greene and Tischler, 1976). The fact that the S34N cells grew slower suggested that these cells may favor cell differentiation, consistent with the observation that S34N indeed enhanced the neurite outgrowth (FIG. 4A). The faster growth rate of the Q79L cells correlated well with the block in neurite outgrowth (FIG. 4A). Furthermore, that the Q79L cells grew well indicated that the expression of Rab5:Q79L did not cause cell death or other pleiotropic cytopathic effects, and the inability of these cells to grow neurites was likely a physiological consequence of Rab5:Q79L.

Figure 5:
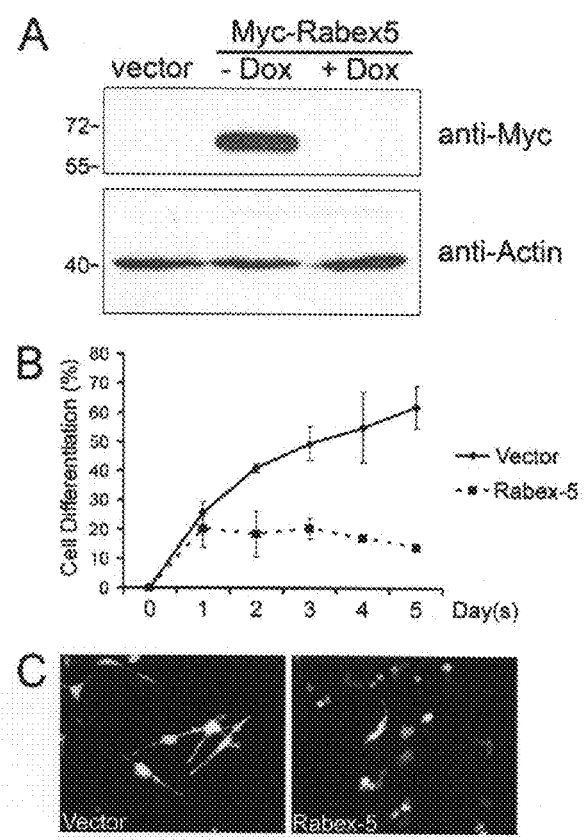
FIG. 5 illustrates Rabex-5-mediated inhibition of neurite outgrowth in PC12 cells. (A) Immunoblot of Myc-Rabex-5 expressed in PC12 cells via the pBI vector in the absence (−) or presence (+) of Dox as indicated. Vector alone served as a negative control. Molecular mass standards (in kilodaltons) are indicated on the left. (B) Comparison of neurite outgrowth in control PC12 cells transfected with vector and cells expressing Myc-Rabex-5 as indicated, in the absence of Dox to induce protein expression. On addition of 50 ng/ml NGF, neurite outgrowth was quantified each day as described in FIG. 1 legend. More than 150 transfected cells were measured in each case, and SEMs were obtained from three independent experiments. (C) Fluorescence microscopy images of control cells (vector) and cells expressing Myc-Rabex-5 after 5-d treatment with NGF.

Transient Expression of Rabex-5 Blocks NGF-mediated Neurite Outgrowth. Constitutive activation of Rab5 exhibited negative effect on NGF-induced neurite outgrowth, as evidenced by the Rab5:Q79L results (FIGS. 1-4). To test further the specific role of Rab5 in the neurite outgrowth process, Rabex-5, a specific Rab5 GEF that activates Rab5, was expressed in PC12 cells, and it was determined whether it may exhibit the same negative effect on neurite outgrowth as Rab5:Q79L. The Myc-tagged Rabex-5 was expressed via the pBI vector and was detected by immunoblot analysis with the anti-Myc antibody (FIG. 5A). The pBI/EGFP vector was cotransfected to mark the transfected cells with EGFP expression. On NGF treatment, the transfected cells were identified by fluorescence microscopy, and neurite outgrowth was scored each day for 5 days. Like Rab5:Q79L, the expression of Rabex-5 blocked neurite outgrowth (FIGS. 5, B and C). Interestingly, it took 2-3 d for Rabex-5 to show inhibitory effect in comparison with the more acute inhibition by Rab5:Q79L, possibly due to the fact that the Rabex-5 effect is manifested via its activation of endogenous Rab5 and is less direct than the constitutive active Rab5:Q79L itself.

NGF Rapidly Down-Regulates Rab5 Activity. The data so far indicated that high Rab5 activity (Rab5:Q79L and Rabex-5) blocked neurite outgrowth. Low Rab5 activity (Rab5:S34N) enhanced this process. Thus, the possibility that NGF signaling itself may downregulate Rab5 activity during neurite outgrowth and differentiation was directly examined.

As a GTPase, Rab5 activity in the cell is reflected by the level of active GTP-bound Rab5, which was determined by developing and using a GST pull-down assay. The assay was based on the specific binding of Rab5-GTP by the R5BD of Rabaptin5 (a Rab5 effector) (Stenmark et al., 1995; Zhu et al., 2004). GST-R5BD fusion protein was made and used to pull-down Rab5-GTP in PC12 cell lysates, followed by immunoblot analysis with a Rab5 antibody to determine the relative amount of Rab5-GTP. Endogenous Rab5-GTP level was too low to be detected in this assay; thus, the cells were transfected with pBI/Rab5 to overexpress Rab5. As positive and negative controls, Rab5:Q79L and Rab5:S34N mutants were expressed, respectively. Rab5:Q79L showed the most robust pull-down signal that reflected high level of GTPbound form, consistent with its defect in GTP hydrolysis (FIG. 6A). WT Rab5 also showed pull-down signal but at a level sevenfold lower than that of Rab5:Q79L (FIG. 6A). In contrast, Rab5:S34N showed no pull-down signal, consistent with its defect in GTP binding (FIG. 6A). These results demonstrated the feasibility of the GST-R5BD pull-down assay in determining the relative amount of Rab5-GTP in the cell.

To determine whether NGF may regulate the Rab5-GTP level in PC12 cells, NGF was added to the cells overexpressing Rab5:WT for different times, followed by the pull-down assay to determine the amount of Rab5-GTP at each time point. NGF rapidly decreased the Rab5-GTP level by fivefold within 5 min and kept the low level for at least 1 h (FIG. 6B). This correlated with the activation and endocytosis of TrkA (Jullien et al., 2002). Because the activation of TrkA is transient and it is inactivated by dephosphorylation after endocytosis, Rab5 activity was examined at later time points, and it was found that the steady-state Rab5-GTP level recovered to a level slightly higher than the control by 24- and 48-h post-NGF treatment (FIG. 6B). The transient reduction of Rab5-GTP level is likely underestimated, considering the overexpression of Rab5. In normal cells without Rab5 overexpression, NGF signaling may lead to a more complete inactivation of endogenous Rab5.

Figure 7:
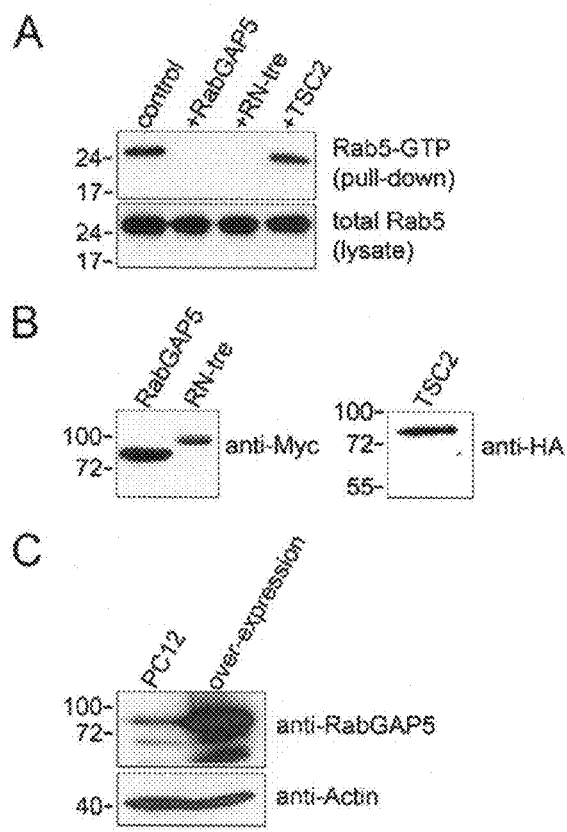
FIG. 7 illustrates RabGAP5 activity and expression in PC12 cells. (A) PC12 cells were cotransfected with pBI/Rab5WT, and each of the potential Rab5 GAPs (with Myc or HA tag and in pcDNA3) as indicated. Shown are the Rab5-GTP levels (Rab5-GTP) and total amount of Rab5 (total Rab5) in these cells, determined by the GST-R5BD pulldown assay described in FIG. 6. Control cells (control) were transfected with pBI/Rab5WT and empty pcDNA3 vector. Molecular mass standards (in kilodaltons) are indicated on the left. (B) Additional controls, indicating that each putative GAP protein is indeed expressed in the transfected cells by immunoblot analysis of cell lysates with anti-Myc and anti-HA antibodies for detection of Myc-tagged RabGAP5, RN-tre, and HA-tagged TSC2, respectively. Molecular mass standards (in kilodaltons) are indicated on the left of each panel. (C) Endogenous (PC12) and overexpressed RabGAP5 in control and transfected PC12 cells by immunoblot analysis with the anti-RabGAP5 antibody, as indicated. Immunoblot of actin (as indicated) on the same membrane serves as the loading control.

RabGAP5 Activity in PC12 Cells: NGF-mediated downregulation of Rab5 may require TrkA to recruit a Rab5 GAP, which inactivates Rab5 by stimulating GTP hydrolysis. The Rab5-specific GAP (RabGAP5) was recently identified (Haas et al., 2005). In addition, other proteins such as RN-tre (Lanzetti et al., 2000) and TSC2 (Xiao et al., 1997) were also reported to have GAP activity toward Rab5. Thus, it was examined whether these GAPs can actually down-regulate Rab5 in vivo in PC12 cells. Each of the GAPs with Rab5:WT were coexpressed in PC12 cells, and their effect on the level of Rab5-GTP was determined by the GSTR5BD pull-down assay. RabGAP5 and RN-tre showed Rab5 GAP activity and efficiently reduced Rab5-GTP level in the cell (FIG. 7A). In contrast, TSC2 showed no Rab5 GAP activity in the cell (FIG. 7A). In each case, the total Rab5 expression was the same (FIG. 7A). In additional control experiments, the expression of each GAP protein (tagged with either Myc or HA epitope) was confirmed by immunoblot analysis with anti-Myc and anti-HA antibodies (FIG. 7B). Importantly, the RabGAP5 protein was abundant in PC12 cells, and it was possible to detect endogenous Rab-GAP5 by immunoblot analysis with the affinity-purified anti-RabGAP5 antibody (Haas et al., 2005). The antibody recognized a major protein band at □75 kDa with two smaller minor species (FIG. 7C). The 75-kDa protein correlated with the full-length RabGAP5 (Haas et al., 2005), whereas the smaller proteins were likely degradation products. Overexpression of RabGAP5 in these cells, via transfection of a plasmid containing rat RabGAP5 cDNA, enhanced production of the 75-kDa protein species (FIG. 7C), confirming that it is indeed RabGAP5.

Figure 8:
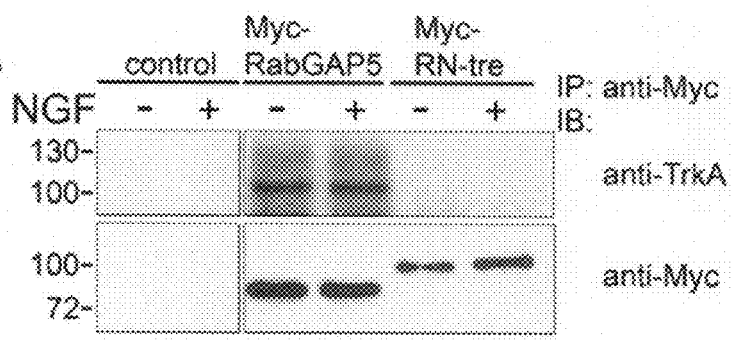
FIG. 8 illustrates co-immunoprecipitation (CoIP) of RabGAP5 with TrkA. (A) PC12 cell lysates containing coexpressed TrkA and each of the Myc-tagged GAPs (as indicated) were immunoprecipitated by anti-Myc antibody-conjugated Sepharose beads, followed by SDS-PAGE and immunoblot (IB) analysis with anti-TrkA and anti-Myc antibodies, respectively. Control cells expressed TrkA only without the GAPs. Top, association of TrkA with immunoprecipitated RabGAP5 but not with RN-tre. The NGF treatment was for 5 min (+). Bottom, controls indicating the successful immunoprecipitation of each of the Myctagged GAPs. Molecular mass standards (in kilodaltons) are indicated on the left of each panel. (B) Same experiment as described in A except that RabGAP5 truncation mutants were expressed instead of their WT counterparts. RGAP5N, N-terminal half (residues 1-440) of RabGAP5; RGAP5C, C-terminal half (residues 441-749) of RabGAP5. (C) Same experiment as described in A and B except that anti-pTrkA instead of anti-TrkA antibody was used in the immunoblot analysis, as indicated. (D) Schematic illustration of the RabGAP5 structure. Locations of TBC, SH3, and RUN domains are indicated, and the residue numbers mark the truncation mutants.
Figure 8:
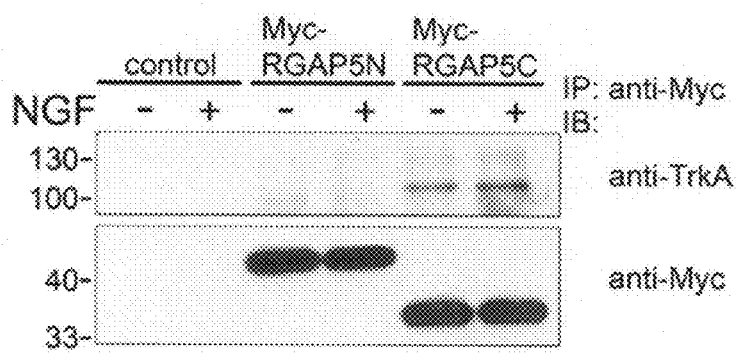
Figure 8:
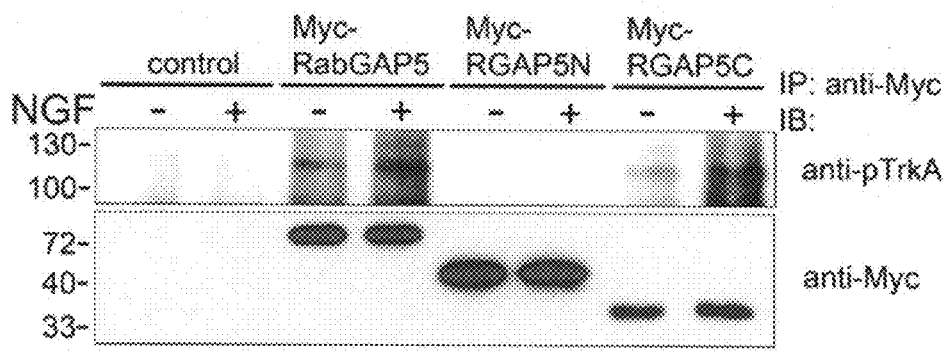
Figure 8:
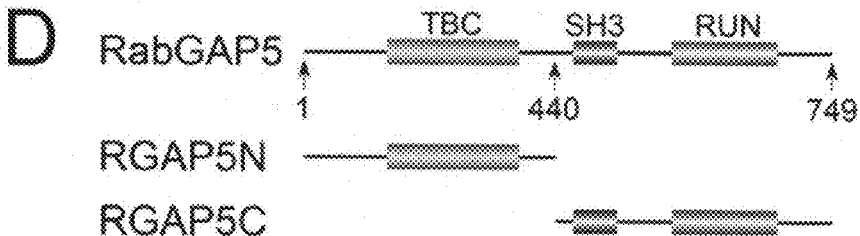

RabGAP5 Is Associated with TrkA: Next, it was determined whether RabGAP5 or RN-tre is associated with TrkA by coIP assays. Each GAP (containing the Myc tag) was coexpressed with TrkA in PC12 cells. The cells were then either treated or not treated with NGF, followed by cell lysis and incubation with Myc antibody-conjugated Sepharose beads to immunoprecipitate the GAP proteins. Total TrkA or pTrkA associated with the GAP proteins was determined by immunoblot analysis with the anti-TrkA or anti-pTrkA antibody. It was found that RabGAP5 was associated with TrkA, whereas RN-tre was not (FIG. 8A). Although the total amount of TrkA associated with RabGAP5 seemed not changed upon NGF treatment (FIG. 8A), the association of activated and pTrkA was markedly enhanced upon NGF treatment (FIG. 8C). RabGAP5 contains several functional domains, with the GAP (or Tre2/Bub2/Cdc16 [TBC]) domain in the N-terminal half and the Scr homology (SH)3 and RPIP8/UNC14/NESCA (RUN) domains in the C-terminal half (Haas et al., 2005) (FIG. 8D). To dissect further the domains involved in the association with TrkA, Myc-tagged RabGAP5-N (residues 1-440) and RabGAP5-C (residues 441-749) were made and expressed in PC12 cells, and it was determined which one would associate with TrkA by the coIP assay. The results showed that only the C-terminal half (RabGAP5-C), which contains SH3 and RUN domains, was associated with TrkA (FIG. 8B). In this case, an increase in the total amount of TrkA associated with RabGAP5-C was detected upon NGF treatment (FIG. 8B). More profound increase was seen in the association of pTrkA and RabGAP5-C upon NGF treatment (FIG. 8C), consistent with the results on the association of pTrkA with full-length RabGAP5 (FIG. 8C).

Figure 9:
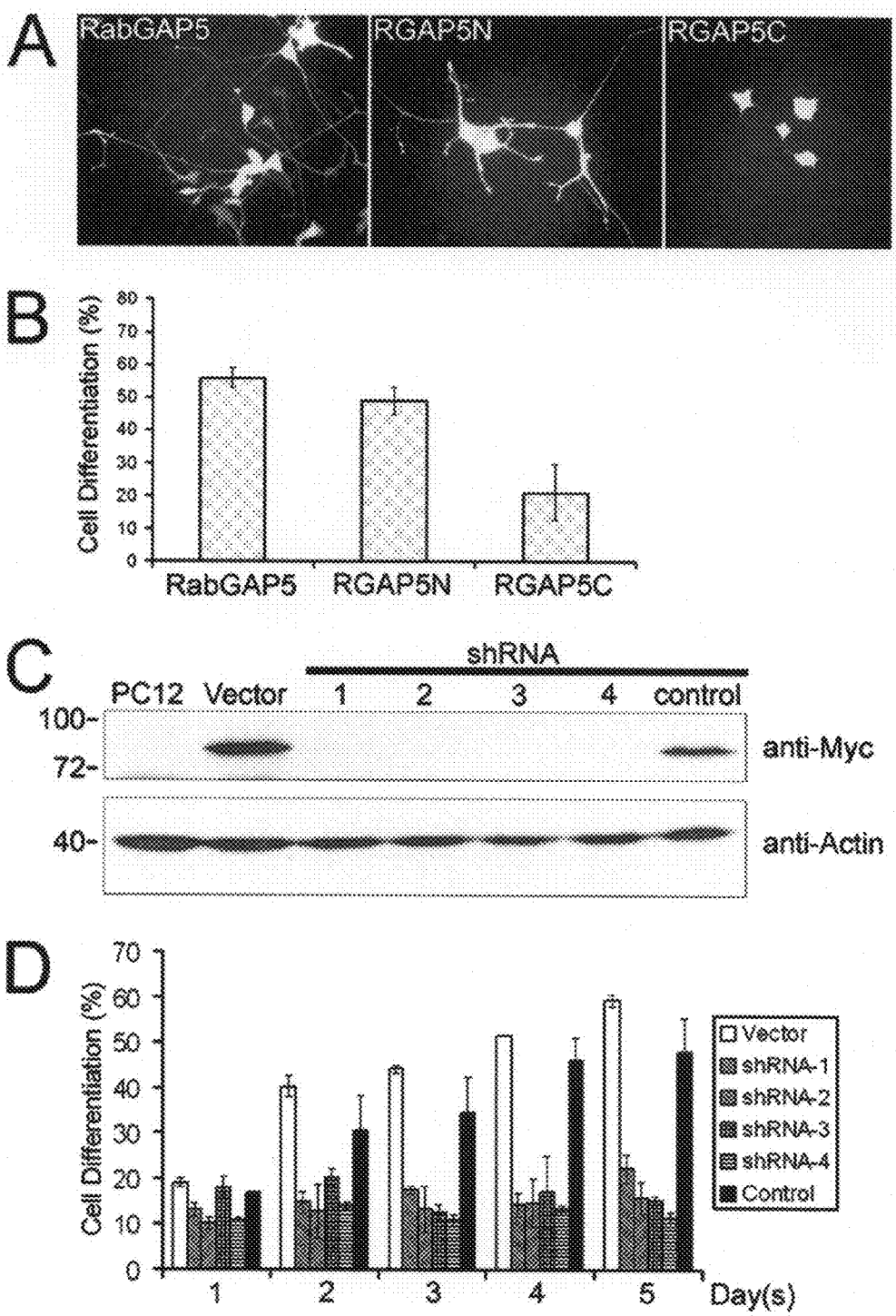
FIG. 9 illustrates inhibition of NGF-induced neurite outgrowth by RabGAP5 truncation mutant and RNAi. (A) Fluorescence microscopy images of the cells after a 6-d treatment with 50 ng/ml NGF and with or without expression of RabGAP5 and the two truncation mutants, as indicated. (B) Quantification of the results from A. The percentage of differentiated cells was determined from >200 transfected cells expressing EGFP and the indicated RabGAP5 proteins in each case. Error bars represent SEM of three independent experiments. (C) Inhibitory effect of RabGAP5 RNAi on the expression of Myc-RabGAP5 in PC12 cells by immunoblot analysis with the anti-Myc antibody, as indicated. Cells were either not transfected (lane PC12) or cotransfected with pcDNA3/Myc-RabGAP5 (rat) and each of the pSUPER constructs expressing shRNAs for rat RabGAP5 (1-4), its human counterpart (control), or the empty vector (vector). Immunoblot of actin serves as the loading control. Molecular mass standards (in kilodaltons) are indicated on the left. (D) Inhibitory effect of RabGAP5 RNAi on NGF-induced neurite outgrowth. Cells were cotransfected with pBI/EGFP and each of the pSUPER constructs as indicated, followed by neurite outgrowth assays described in A and B.

RabGAP5 Truncation Mutant or Knockdown via shRNA Blocks NGF-mediated Neurite Outgrowth. To further examine the relevance of RabGAP5 in NGFmediated neurite outgrowth, full-length and truncated RabGAP5 proteins were expressed in PC12 cells, and the effect on neurite outgrowth was determined (FIG. 9), with the same assay as was used for determining the Rab5 effect (FIG. 1). Each RabGAP5 protein was coexpressed with EGFP, which helped identify the transfected cells via fluorescence microscopy. Like the dominant-negative Rab5 mutants (FIG. 1), full-length RabGAP5 showed no inhibitory effect on NGFinduced neurite outgrowth (FIG. 9). It did not further enhance neurite outgrowth either, suggesting that if required, it is not rate limiting in PC12 cells. To determine whether abrogation of endogenous RabGAP5 function may affect neurite outgrowth, truncated RabGAP5 proteins (RabGAP5-N and RabGAP5-C) were expressed in PC12 cells, and then NGF-mediated neurite outgrowth was determined. Although RabGAP5-N had little effect, RabGAP5-C greatly reduced the neurite outgrowth from 60 to 20%, (FIG. 9), possibly by competing with endogenous RabGAP5 for association with TrkA. To further demonstrate the requirement of RabGAP5 in neurite outgrowth, PC12 cells were transfected with pSUPER constructs that expressed shRNAs to knock down RabGAP5 expression. The four shRNAs targeting different regions in rat RabGAP5 all effectively knocked down coexpressed myc-RabGAP5 (rat cDNA) levels, whereas a shRNA targeting human RabGAP5 had only a small (but consistent) effect on the myc-RabGAP5 expression in comparison with the pSUPER vector control (FIG. 9). The effect on endogenous RabGAP5 was difficult to assess with the immunoblot assay because of the low transfection efficiency in PC12 cells. Importantly, the transfected cells expressing the four rat shRNAs, as identified by coexpression of EGFP, showed 50% or more reduction in NGF-induced neurite outgrowth, with shRNA4 being the most potent inhibitor (FIG. 9), whereas the control human shRNA had little effect in comparison with the vector control (FIG. 9).

RN-tre was also examined in this regard, and it was found that expression of either WT or the GAP-dead RN-tre:R150A mutant (Lanzetti et al., 2000) induced severe cell rounding (data not shown). Whereas this RN-tre effect may be associated with its growth-promoting properties, it is not what is expected of a Rab5 GAP in facilitating neurite outgrowth. In addition, the RN-tre effect is independent of its GAP activity and thus is likely mediated through a function other than Rab5. Together with the fact that RN-tre is not associated with TrkA (FIG. 8A), it was concluded that RN-tre is not involved in NGF signaling-mediated Rab5 inactivation and neurite outgrowth.

Discussion

Endocytosis is essential for NGF-mediated neurite outgrowth and differentiation in PC12 cells (Grimes et al., 1996; Zhang et al., 2000). NGF signaling is initiated when it binds to its receptor TrkA at the cell surface, leading to transient activation of the Ras/MAPK pathway and phosphoinositide 3-kinase that promotes cell survival (Zhang et al., 2000). The NGF-TrkA complex is then endocytosed into the cell and found on the so-called signaling endosomes (Grimes et al., 1996) where TrkA is suggested to recruit new adaptors and to activate additional signaling processes to induce neurite outgrowth (York et al., 1998; Meakin et al., 1999). The biogenesis of signaling endosomes is not well understood. Although signaling endosomes contain early endosomal markers such as Rab5 (Delcroix et al., 2003), they are involved in long-distance retrograde transport of NGF in axons and have a much longer lifetime than conventional early endosomes, implying that Rab5 activity needs to be suppressed at this stage to avoid fusion with endosomes. Rink et al. (2005) recently described a model on the dynamic nature of the early endosomal network (EEN) and the transition to late endosomes. Rab5-dependent early endosome fusion is necessary for the entry to the EEN where cargoes are concentrated before the progression to late endosomes.

Figure 10:
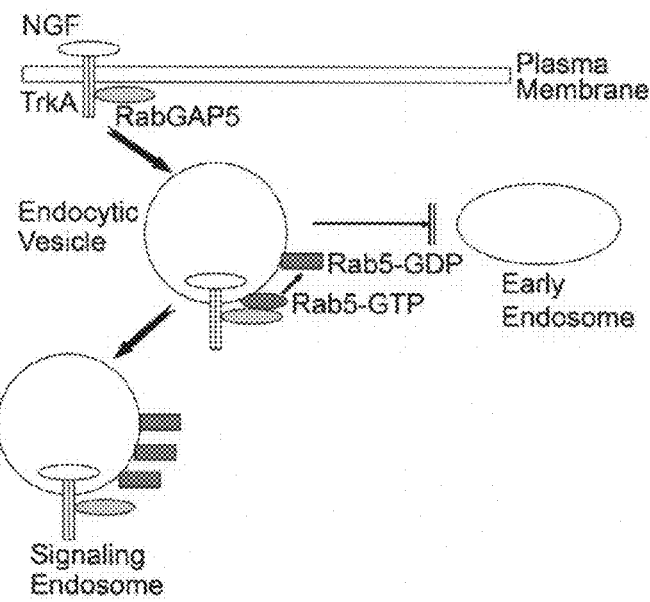
FIG. 10 depicts a model of NGF/TrkA-mediated Rab5 inactivation and establishment of signaling endosomes. NGF binds TrkA and induces its endocytosis. TrkA-associated RabGAP5 inactivates Rab5 by promoting its GTP hydrolysis. As a result, the TrkA-containing endocytic vesicles cannot fuse with early endosomes and enter the endocytic pathway. This population of TrkA-containing endocytic vesicles is thus diverted from the conventional endocytic pathway and specializes to become the signaling endosomes.

These data shed light on the biogenesis of signaling endosomes (FIG. 10). NGF binding and signaling induce endocytosis of its receptor TrkA. RabGAP5 associates with TrkA, such that the TrkA-containing endocytic vesicles have low Rab5 activity and thus less opportunity to fuse with early endosomes and enter the EEN. As a result, the TrkA-containing vesicles are diverted from the EEN and specialize to become signaling endosomes, which serve as a platform for signaling processes leading to neurite outgrowth and differentiation.

The model is supported by several lines of evidence. First, low Rab5 activity (Rab5:S34N) facilitates NGF signaling and neurite outgrowth, whereas high Rab5 activity (Rab5:Q79L and Rabex-5) inhibits this process. Second, high Rab5 activity (Rab5:Q79L) diminishes intracellular NGF signaling by rapid dephosphorylation of internalized pTrkA, possibly via gaining access to endosome-associated phosphatases, whereas low Rab5 activity (Rab5:S34N) sustains intracellular NGF signaling by blocking endosome fusion and consequently the access to the phosphatases. Third, NGF signaling leads to down-regulation of Rab5 activity as evidenced by the reduction of Rab5-GTP level in PC12 cells. Fourth, Rab-GAP5 is found to be associated with TrkA as evidenced by coIP assays. Finally, RabGAP5 RNAi and truncation mutant inhibit NGF-induced neurite outgrowth, strongly suggesting the requirement of RabGAP5 and thus down-regulation of Rab5 in this process. Other Rab5-related functions such as regulation of membrane ruffles (Lanzetti et al., 2004), could promote neurite growth. Although this possibility cannot be ruled out, it is inconsistent with the data that show Rab5:S34N, which should inhibit Rab5-mediated ruffles, actually increases NGF signaling and neurite outgrowth.

RabGAP5 is associated with TrkA and pTrkA, although it is yet to be determined whether pTrkA has higher affinity. This physical coupling can ensure that each TrkA-containing endocytic vesicle also contains RabGAP5, which should suppress Rab5 activity and prevent the vesicle from entering the EEN and endocytic pathway. In this context, the observation that NGF rapidly reduces the Rab5-GTP level may be explained if NGF induces new recruitment of RabGAP5 to pTrkA and/or NGF-induced TrkA endocytosis brings the associated RabGAP5 with it from the plasma membrane into endocytic vesicles where most Rab5 molecules are targeted and activated (Ullrich et al., 1994), leading to the approximation of RabGAP5 to its substrate, i.e., Rab5-GTP. It is also possible that NGF may enhance the GAP activity of Rab-GAP5 already bound to TrkA, although such an activation mechanism has not been described for a Rab GAP.

The fate of signaling endosomes remains an open question. Because Rab5 is retained on signaling endosomes (Delcroix et al., 2004), the possibility exists that they may eventually reenter the EEN and endocytic pathway upon reactivation of Rab5, which requires the recruitment and action of Rab5 GEFs, e.g., Rabex5 (Horiuchi et al., 1997) and RIN proteins (Tall et al., 2001; Kajiho et al., 2003), to overcome the GAPs. In support of this contention, localized balance of GEFs and GAPs is shown to regulate the activities of Ras-like small GTPases in different compartments (Mochizuki et al., 2001; Bivona et al., 2003). In addition, the data show that NGF-induced down-regulation of Rab5 occurs in the initial phase, but cellular Rab5 activity (i.e., the Rab5-GTP level) recovers later, corresponding to the activation and inactivation phases of TrkA. Furthermore, TrkA does eventually reach lysosomes after NGF-induced endocytosis, despite the diversion into signaling endosomes (Zhou et al., 1995; Jullien et al., 2002). In this context, a remarkable contrast was noticed between NGF signaling that promotes cell differentiation and EGF signaling that promotes cell growth and proliferation. NGF signaling suppresses Rab5 via the RabGAP5 to help establish the signaling endosomes and sustain the differentiation signals (this study), whereas epidermal growth factor signaling enhances Rab5 activity via the Rab5 GEFs to accelerate the entry into the EEN and endocytic pathway (Tall et al., 2001). In this regard, Rab5 may be considered as a switch in cell fate decision: differentiation versus proliferation.

EXAMPLE 2

Rabex-5 is a guanine nucleotide exchange factor (GEF) for Rab5 (Horiuchi et al., 1997), a small GTPase regulating early endosome fusion and endocytosis (Gorvel et al., 1991; Bucci et al., 1992; Li et al., 1994; Hoffenberg et al., 1995; Li and Liang, 2001). Interestingly, Rabex-5 was originally purified as a soluble complex with Rabaptin-5, and immunodepletion of this complex can reduce early endosome fusion in vitro (Horiuchi et al., 1997). Rabex-5 itself shows very little GEF activity in vitro, and it requires interaction with Rabaptin-5 to gain activity (Esters et al., 2001; Lippe et al., 2001). Furthermore, the core GEF domain (Vps9 domain plus the upstream helical bundle and the downstream α-helix, residues 132-391) of Rabex-5 is also much more active than the full-length protein in vitro biochemical assays (Delprato et al., 2004). It is unclear why the full-length Rabex-5 has such low GEF activity in vitro and how interaction with Rabaptin-5 can stimulate this activity. This could be due to a folding or conformational problem of the full-length Rabex-5 in vitro or it could reflect a physiologically relevant regulatory mechanism in the cell.

Rabex-5 contains multiple functional domains (Delprato et al., 2004). A coiled-coil domain downstream of the GEF domain may mediate the binding to Rabaptin-5, as shown in a yeast two-hybrid assay (Mattera et al., 2006), whereas a $Zn^{2+}$ finger (ZnF) domain at the N terminus is shown to bind ubiquitin (Lee et al., 2006; Mattera et al., 2006; Penengo et al., 2006). Recently, Rabex-5 (also called Rab-GEF1) knockout mice have been generated, and they die early and develop severe skin inflammation (Tam et al., 2004). Mast cells isolated from these Rabex-5-deficient mice show enhanced stem cell factor/c-Kit-mediated signal transduction and biological responses (Kalesnikoff et al., 2006). It is not yet clear whether these effects are related to the Rabex-5 GEF activity for Rab5. In addition to Rabex-5, there are other Vps9 domain-containing proteins, e.g., the RIN proteins (Tall et al., 2001; Saito et al., 2002), which may contain signal transduction-activated Rab5 GEF activity (Carney et al., 2006).

In this Example, Rabex-5 function was investigated in vivo, and the following questions were specifically addressed: 1) Is the full-length Rabex-5 protein itself active as a Rab5 GEF in the cell? 2) Is the GEF domain itself active as a Rab5 GEF in the cell? 3) What is the role of Rabaptin-5 in Rabex-5 GEF activity? and 4) Can Rabex-5 target to early endosomes independently of Rabaptin-5 in the cell? If so, which domain is responsible? The data presented herein identify a novel mechanism in the membrane targeting and function of Rabex-5 in the cell, and they clarify unresolved issues by reconciliation with in vitro studies.

Materials and Methods

Plasmids: pGEX-6p-1, pGEX-4T-2, and pGEX-3X were purchased from GE Healthcare (Little Chalfont, Buckinghamshire, United Kingdom). pET-11a, pET-15b, and pET28a were from Novagen (Madison, Wis.). pMAL-2c was from New England Biolabs (Natick, Mass.). pBI was from BD Biosciences (San Jose, Calif.).

Protein Expression and Purification: Rabex-5 cDNA (*Bos taurus*, NCBI accession no. NM_174591) and truncated fragments were cloned into the pGEX and pMAL vectors for expression as glutathione S-transferase (GST) and maltose-binding protein (MBP) fusion proteins or into the pET-28a vector for expression as His-tagged proteins. Rabaptin-5 cDNAs were cloned into pET-15b for expression as His-tagged proteins or into pET-11a vectors for expression as free proteins (Zhu et al., 2004b). The plasmid constructs were transformed into the *Escherichia coli* strain BL21 (DE3), and the expressed proteins were purified as soluble proteins by following the procedure described previously (Zhu et al., 2004a). To purify Rabex-5-Rabaptin-5 complexes, pET-28a/Rabex-5(135-480) and pET-11a/Rabaptin-5(572-641) were cotransformed into BL21(DE3), and the transformed bacteria were grown in LB medium containing both ampicillin (60 mg/l) and kanamycin (30 mg/l). Protein expression was induced by adding 0.1 mM isopropyl β-D-thiogalactoside at $OD_{600}$ of 0.6, and the bacterial cultures were allowed to grow for another 15 h at 16° C., before being harvested and lysed with lysozyme. Recombinant proteins were purified from the supernatants of cell lysates by affinity His-Select resin (Sigma-Aldrich, St. Louis, Mo.). The eluted complex was cleaved by thrombin to remove the His-tag and further purified with Resource Q ion-exchange chromatography (GE Healthcare). The purified complex was analyzed by SDS-polyacrylamide gel electrophoresis (PAGE) (20% gel) and visualized by Coomassie brilliant blue staining.

GST and MBP Pull-Down Assays: Recombinant GST- and MBP-Rabex-5 fusion proteins were immobilized on glutathione Sepharose-4B (GE Healthcare) and Amylose (New England Biolabs) resins, respectively. Five micrograms of recombinant Rabaptin-5 proteins were incubated with the resin containing 5 pg of GST- or MBP-Rabex-5 as indicated for 30 min in the binding buffer (200 μl) according to the manufacturer's instructions. The final concentration of each protein was <2 μM for detection of specific binding. The resins were subsequently washed three times with phosphate-buffered saline (PBS) and resuspended in 20 μl of SDS sample buffer. The samples were subjected to 20% SDS-PAGE analysis, and the proteins were visualized by Coomassie brilliant blue staining.

Guanosine 5'-O-(3-thio)triphosphate (GTPγS) Loading Assay; GST-Rab5 was purified with glutathione Sepharose-4B resin in PBS containing 10 mM $MgCl_2$ and 1 mM GDP to keep GDP on Rab5. Rab5-GDP was then separated from GST and released into the supernatant by thrombin, which was later removed by benzamidine-Sepharose (GE Healthcare). The protein was dialyzed in the binding buffer (50 mM Tris-HCl, pH 7.4, 150 mM NaCl, 5 mM $MgCl_2$, 1 mM EDTA, and 1 mM dithiothreitol). A modified version of the filter binding assay (Lippe et al., 2001) was used to determine the [35S] GTPγS binding rate of Rab5-GDP, which reflected its nucleotide exchange rate. Briefly 1 μM Rab5-GDP was incubated with 2 μM [$^{35}$S]GTPγS (GE Healthcare) in 100 μl of the binding buffer in the absence or presence of 0.1 μM of various Rabex-5 fragments or Rabex-5-Rabaptin-5 complexes. At indicated times, samples were taken and filtered through a hemagglutinintype nitrocellulose membrane (0.45 μm; Millipore, Billerica, Mass.) by using a vacuum manifold. After washing with 2 ml of the binding buffer, the membrane was dried and [$^{35}$S]GTPγS retained on the membrane was quantified with a liquid scintillation counter.

Mammalian Cell Cultures and Transfection: Baby hamster kidney (BHK)-21 cell monolayers were grown in 35-mm culture dishes with 3 ml of α-minimal essential medium containing 10% fetal bovine serum (Invitrogen, Carlsbad, Calif.). Cells were transfected with the plasmid constructs capable of expressing Rabex-5, Rabaptin-5, or Rab5 proteins as indicated via the Lipofectamine 2000-mediated procedure (Invitrogen), and they were incubated at 37° C. for 24 h. The expression plasmids used included pcDNA3 (Invitrogen) and pBI (BD Biosciences). The pBI vector requires cotransfection with pTet-Off, and they can express two cloned proteins simultaneously. Protein expression was confirmed by immunoblot analysis and intracellular localization and endosomal morphology were determined by confocal fluorescence microscopy (see below).

Immunoblot Analysis: Cells were lysed in 1% SDS (200 μl/dish), and the lysates were sheared to reduce the stickiness by passing through a 26-gauge needle five times with a 1-ml syringe, followed by SDS-PAGE (12% gel) and immunoblot assay by using the enhanced chemiluminescence reagents (GE Healthcare). The primary antibodies used in these assays included anti-MYC monoclonal antibody (mAb) (Sigma-Aldrich), anti-FLAG mAb (Sigma-Aldrich), and anti-Rabaptin-5 antibody (BD Biosciences) as indicated.

Confocal Fluorescence Microscopy: A Leica confocal laser scanning microscope with Ar-488 and Kr-568 laser excitation in the Flow and Image Lab on campus (University of Oklahoma, Oklahoma City, Okla.) was used, and a procedure described previously (Li and Liang, 2001) was followed. Briefly, BHK-21 cells were grown on coverslips and transfected with pBI and/or pcDNA3 constructs expressing various Rabex-5, Rabaptin-5, or Rab5 proteins as indicated. At 24 h after transfection, the cells were processed for microscopy. Some of the proteins were expressed as green fluorescent protein (GFP) (enhanced green fluorescent protein; BD Biosciences) or red fluorescent protein (RFP) (ds-Red monomer; BD Biosciences) fusion proteins. For these fluorescent protein-tagged proteins, cells were rinsed three times with PBS and fixed for 20 min with 4% paraformaldehyde (wt/v in PBS) at room temperature. The coverslips were then mounted in PBS on glass slides and viewed with the microscope. For Myc-tagged proteins, indirect immunofluorescence microscopy was performed to identify the proteins. In this case, after fixation (see above), the cells were permeabilized with 0.05% saponin (in PBS) for 15 min and incubated with the anti-Myc antibody (Sigma-Aldrich) for 60 min in PBS containing 1% bovine serum albumin. Cells were rinsed three times with PBS to remove unbound primary antibody, followed by incubation with the secondary antibody (goat anti-mouse immunoglobulin G conjugated with Alexa568; Invitrogen) for 60 min. The coverslips were rinsed, mounted, and viewed as described above.

Subcellular Fractionation: BHK-21 cell monolayers in 35-mm dishes were grown and transfected as described above. At 24 h after transfection, the cells were rinsed with ice-cold PBS and scraped into 250 µl of 100 mM Tris-HCl, pH 7.4, containing the protease inhibitor cocktail (Sigma-Aldrich) with a cell scraper (Fisher Scientific, Pittsburgh, Pa.). The cells were then homogenized by passing through a 26-gauge needle attached to a 1-ml syringe 20 times. Cell homogenates were centrifuged at 850 g for 5 min to remove nuclei and cell debris, and postnuclear supernatants were then subjected to ultraspeed centrifugation at 200,000×g for 7 min in a TL-100 centrifuge (Beckman Coulter, Fullerton, Calif.) to separate the membrane fraction (pellet) from the cytosol fraction (supernatant). The membrane pellet was resuspended in the same volume of 100 mM Tris-HCl buffer as the cytosol fraction, and SDS was added to both fractions at a final concentration of 1% (wUv). Proteins in each fraction (10 □l) were analyzed by SDS-PAGE and immunoblot assay as described above.

Results

Biochemical Characterization of the GEF Domain and the Rabaptin-5-binding Domain in Rabex-5. Purified recombinant Rabex-5 showed only weak GEF activity for Rab5 in vitro ($k_{cat}$=0.007 $s^{-1}$), but preformed Rabex-5-Rabaptin-5 complex was much more active (Esters et al., 2001; Lippe et al., 2001). In addition, the core GEF domain (residues 132-391) was also highly active ($k_{cat}$>0.1 $s^{-1}$) (Delprato et al., 2004). These observations might reflect an "autoinhibition" mechanism in which other domain(s) in Rabex-5 blocks the GEF domain activity, and Rabaptin-5 interaction may relieve this inhibition. Alternatively the purified recombinant Rabex-5 used in these in vitro studies might have some folding/conformation problems, and Rabaptin-5 interaction could help regain proper conformation and activity. The results described in this and following sections support the second possibility, and they indicate that Rabex-5 activity in vivo in intact cells can bypass the requirement for Rabaptin-5.

Figure 11:
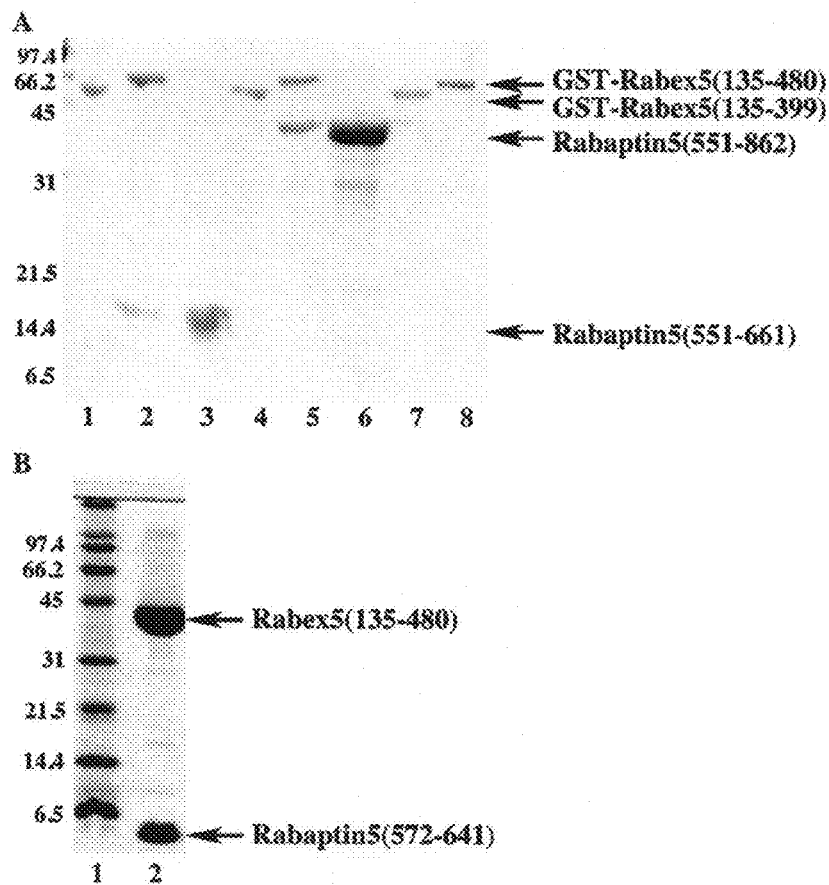
FIG. 11 illustrates the domains involved in Rabex-5 and Rabaptin-5 interaction. (A) The GST-Rabex-5 proteins (5 μg) were used to pull-down purified Rabaptin-5(551-661) (5 μg) in a 200-μl reaction. The bound proteins were analyzed by SDS-PAGE and visualized by Coomassie blue staining. Lane 1, GST-Rabex-5(135-399) incubation with 6-His-Rabaptin-5(551-661); lane 2, GST-Rabex-5(135-480) incubation with 6-His-Rabaptin-5(551-661); lane 3, 6-His-Rabaptin-5(551-661) directly loaded as a control; lane 4, GST-Rabex-5(135-399) incubation with 6-His-Rabaptin-5(551-862); lane 5, GST-Rabex-5(135-480) incubation with 6-His-Rabaptin-5(551-862); lane 6, 6-His-Rabaptin-5(551-862) directly loaded as a control; lane 7, GST-Rabex-5(135-399) directly loaded as a control; lane 8, GST-Rabex-5(135-480) directly loaded as a control. Molecular mass standards (in kilodaltons) are indicated on the left of the panel. (B) 6-His-tagged Rabex-5(135-480) was coexpressed with Rabaptin-5(572-641) in *E coli* BL21 (DE3) and affinity purified with the His-Select resin (Sigma-Aldrich), followed by thrombin cleavage and further purification with Resource Q ion-exchange chromatography (GE Healthcare). Lane 1, molecular mass standards (in kilodaltons); lane 2, purified Rabex-5(135-480) and Rabaptin-5(572-641) complex.

First, the domains involved in the interaction between Rabex-5 and Rabaptin-5 were dissected, and it was found that the Rabaptin-5-binding domain of Rabex-5 blocked its GEF activity in vitro. To identify the interacting domains in Rabex-5 and Rabaptin-5, a number of GST or MBP fusion proteins of Rabex-5 were made and used to pull-down 6-His-tagged Rabaptin-5 proteins. The results showed the interaction between the coiled-coil domain (residues 401-480) of Rabex-5 and the four-helical bundle region (residues 572-641) of Rabaptin-5 (FIG. 11). Rabex-5(135-480), which includes the GEF domain and the downstream coiled-coil domain, formed a complex with Rabaptin-5(551-661) in the pull-down assay (FIG. 11A, lane 2), but Rabex-5(135-399), the GEF domain itself, failed to bind Rabaptin-5(551-661) (FIG. 11A, lane 1). A longer fragment Rabaptin-5(551-862), which contains all the C-terminal sequence, showed the same binding characteristics (FIG. 11A, lanes 4-6). The GST Rabex-5(135-480) and Rabex-5(135-399) resins alone contained no contamination of any Rabaptin-5 proteins, which served as negative controls (FIG. 11A, lanes 8 and 7). Furthermore, MBP-Rabex-5(401-480), the coiled-coil domain alone, was sufficient to bind a 70-amino acid Rabaptin-5(572-641) fragment in the pull-down assay (data not shown). Finally, Rabex-5(135-480) and Rabaptin-5(572-641) were coexpressed in *E. coli*, and it was demonstrated that they were copurified as a complex (FIG. 11B, lane 2). These biochemical results are consistent with a recent report showing similar domain interactions in a yeast two-hybrid assay (Mattera et al., 2006).

Next, the GEF activity of these Rabex-5 domains was examined by determining their effect on [$^{35}$S]GTPγS loading onto Rab5-GDP. The intrinsic nucleotide exchange rate, as reflected by the GTPγS loading rate, was extremely low in the presence of 5 mM $Mg^{2+}$ and served as a negative control in these experiments (FIG. 12A). The GEF domain alone (residues 135-399) strongly stimulated the GTPγS loading of Rab5-GDP (FIG. 12A), consistent with a previous report (Delprato et al., 2004). In this regard, full-length Rabex-5 had little exchange activity (Esters et al., 2001; Lippe et al., 2001). To determine which region in Rabex-5 was responsible for blocking the high activity of the GEF domain, a series of N- and C-terminal extensions to the GEF domain were made. Rabex-5(1-399), which contained the entire sequence N terminal to the GEF domain, showed similar high exchange activity as the GEF domain itself (FIG. 12A). In contrast, Rabex-5(135-480), which contained the coiled-coil domain C terminal to the GEF domain, showed much reduced exchange activity (FIG. 12A), indicating that the coiled-coil domain (i.e., the Rabaptin-5-binding domain) blocked the GEF domain activity. However, the purified Rabex-5(135-480)-Rabaptin-5(572-641) complex (FIG. 11B) exhibited full exchange activity similar to the GEF domain itself (FIG. 12A), indicating that the 70-amino acid Rabaptin-5(572-641) fragment was sufficient to bind the coiled-coil domain (residues 401-480) of Rabex-5 and to overcome its inhibitory effect on the GEF domain.

Figure 12:
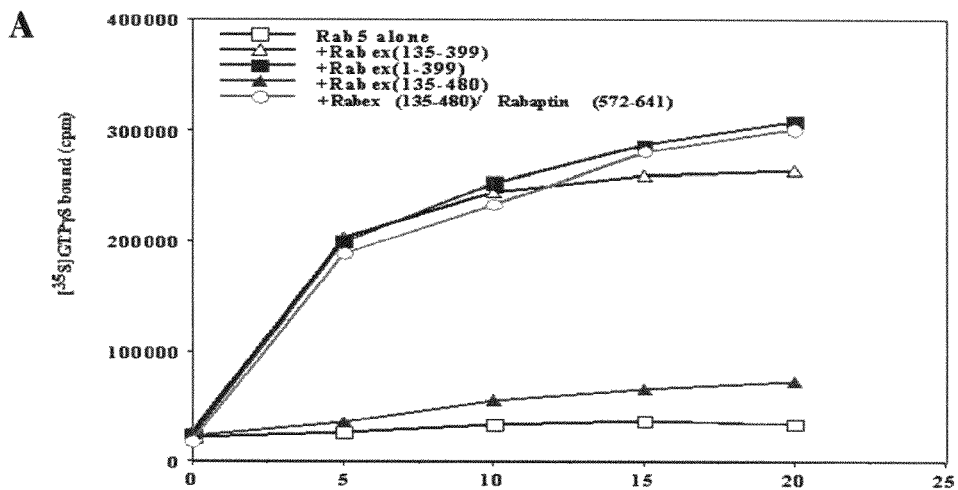
FIG. 12 illustrates GEF activity of Rabex-5 and mutants in vitro and in vivo. (A) Purified Rabex-5(1-399), Rabex-5(135-399), Rabex-5(135-480), and Rabex-5(135-480)/Rabaptin-5(572-641) complex were examined for their ability to stimulate the loading of [$^{35}$S]GTPγS onto Rab5-GDP. The reaction without any of the Rabex-5 constructs (Rab5 alone) served as a negative control. Samples were taken at the indicated times, and the amount of [$^{35}$S]GTPγS bound to Rab5 in each case was determined by the filter binding assay. The results were reproducible in two independent experiments. (B) FLAG-tagged Rab5 was coexpressed in BHK cells with either the pBI vector control or pBI constructs expressing Rabex-5(1-135), Rabex-5, Rabex-5(135-399), Rabex-5(135-480), Rabex-5(135-480)/Rabaptin-5, Rabex-5(81-399) as indicated. Top, amount of Rab5-GTP in each case as determined by GSTR5BD pull-down assay, followed by immunoblot analysis with the anti-FLAG antibody. Middle, total amount of Rab5 in each cell lysate used for the pull-down assay as determined by immunoblot analysis of the lysate directly (1% of the amount for the pull-down assay) with the anti-FLAG antibody. Bottom, expression of the indicated Rabex-5 constructs (Myc-tagged) in the cell as determined by immunoblot analysis with the anti-Myc antibody. Molecular mass standards (in kilodaltons) are indicated on the left. The results were reproducible in three experiments. (C) Ratio of Rab5-GTP over total Rab5 quantified by densitometry of the immunoblots in B. Error bars indicates SEM in three experiments.
Figure 12:
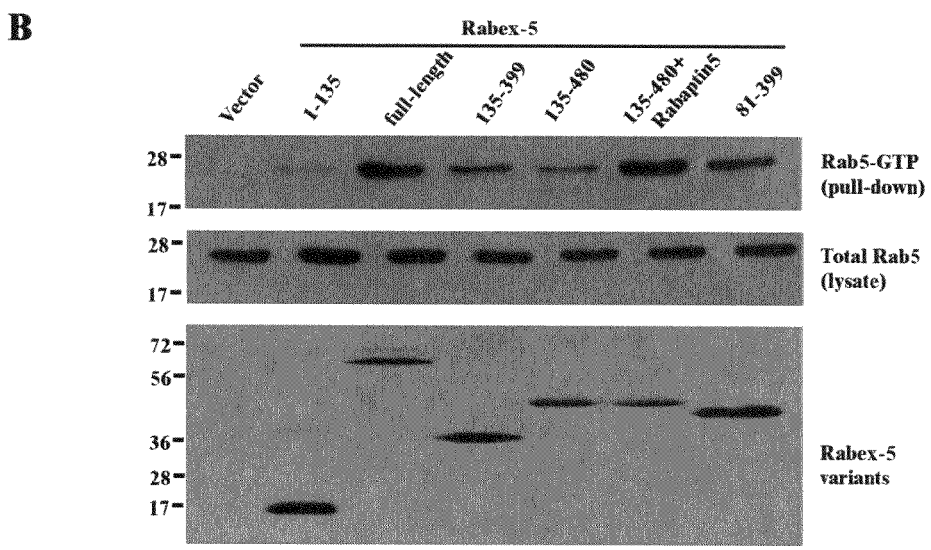
Figure 12:
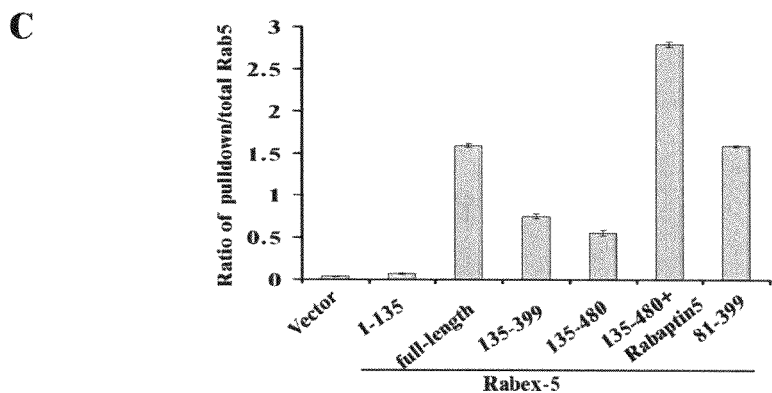

Rabex-5 Activates Rab5 in a Rabaptin-5-independent Manner In vivo. Strikingly, when Rabex-5 and the truncation mutants were examined in mammalian cell cultures and their GEF activity determined in vivo, full-length Rabex-5 showed full activity, whereas Rabex-5(135-399), the GEF domain, showed reduced activity (FIG. 12B), which was in contrast to the results obtained in vitro (FIG. 12A). In this case, Rab5 and Rabex-5 or various Rabex-5 truncation mutants were coexpressed in BHK cells, and the amount of activated GTP-bound Rab5 in cell lysates was determined by pull-down assays by using GST-R5BD (the Rab5-binding domain of Rabaptin-5). Rabex-5 strongly stimulated GTP loading on Rab5, and it increased the Rab5-GTP level in the cell, in comparison with control cells without coexpression of Rabex-5 (FIGS. 12, B and C). In contrast, the GEF domain alone [Rabex-5(135-399)] was much less active than the full-length Rabex-5 (FIGS. 12, B and C), after standardizing Rab5-GTP level with total Rab5 level in each sample. Interestingly, Rabex-5(81-399), which contains an additional sequence N-terminal to the GEF domain, restored the Rab5 GEF activity to a level similar to full-length Rabex-5 (FIG. 12, B and C). Rabex-5(135-480), like Rabex-5(135-399), showed low GEF activity in vivo (FIG. 12, B and C). However, Rabaptin-5, coexpressed from the same vector, significantly increased the activity of Rabex5(135-480) (FIG. 12, B and C). The Rabex-5(1-135) fragment without the GEF domain showed no activity (FIG. 12, B and C).

The data indicate the differences in the ways Rabex-5 activates Rab5 in solution and in the cell where Rab5 is mostly on the endosomal membrane, and these differences can be reconciled if in the cell there is a membrane-targeting step by Rabex-5 before it can act on its substrate, i.e., membrane-associated Rab5-GDP. In addition to the Rabaptin-5-mediated membrane targeting, Rabex-5 may also directly target to early endosomes and activate Rab5. In this regard, the low activity of Rabex-5(135-399) and Rabex-5(135-480) is probably due to defective endosomal targeting, and addition of the endosomal targeting domain, as in Rabex-5(81-399), restores full activity. This direct endosomal targeting may not require Rabaptin-5, because Rabex-5(81-399) does not contain the downstream Rabaptin-5-binding domain. Furthermore, the activity of full-length Rabex-5 may also result from direct membrane targeting rather than from interaction with endogenous Rabaptin-5, which is apparently insufficient to interact with and support Rabex-5(135-480). The residual activity of Rabex-5(135-399) and Rabex-5(135-480) may reflect their activation of the cytosolic fraction of Rab5, because the pull-down assay does not distinguish cytosolic and membrane-bound Rab5-GTP signals. These concepts are further investigated and confirmed by the following microscopy experiments that focus on the early endosome-associated Rab5 activation in the cell.

Figure 13:
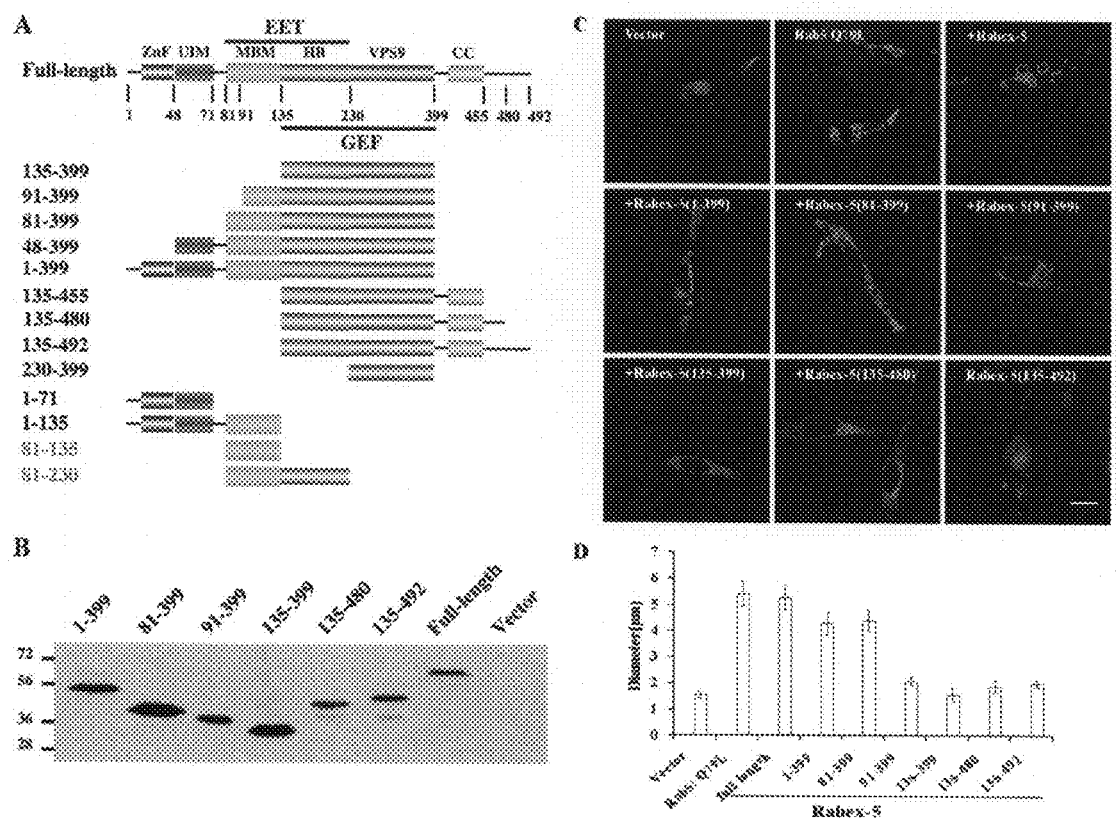
FIG. 13 illustrates expression and activity of Rabex-5 and various truncation mutants in BHK cells. (A) Schematic illustration of the domain structures of full-length Rabex-5 and the truncation mutants used in this and the following experiments. Vps9, Vps9 domain; CC, coiled-coil domain. The arrows and numbers indicate the positions and amino acid residue numbers where the truncations were made. (B) Immunoblot showing the expression of some of the above Rabex-5 constructs with the GEF domain and N-terminal Myc-tag in BHK cells as identified with the anti-Myc antibody. Molecular mass standards (in kilodaltons) are indicated on the left. (C) Confocal fluorescence microscopy images showing the morphological changes of GFP-Rab5-labeled early endosomes in BHK cells coexpressing the indicated Rabex-5 constructs. GFP-Rab5 and GFP-Rab5:Q79L alone (cotransfection with the empty vector) serve as negative (vector) and positive (Rab5:Q79L) controls. Bar, 16 μm. (D) The graph quantifies the experiments described in C, and it shows the different sizes of GFP-Rab5-labeled early endosomes in control cells and cells expressing the indicated Rabex-5 constructs. The diameters of 90 of the largest GFP-Rab5-labeled endosomes in 30 cells were measured in each case, and the graph shows the mean and calculated SEM. All cells measured coexpressed the indicated Rabex-5 constructs as evidenced by immunofluorescence microscopy with the anti-Myc antibody as shown in FIG. 14.
Figure 18:
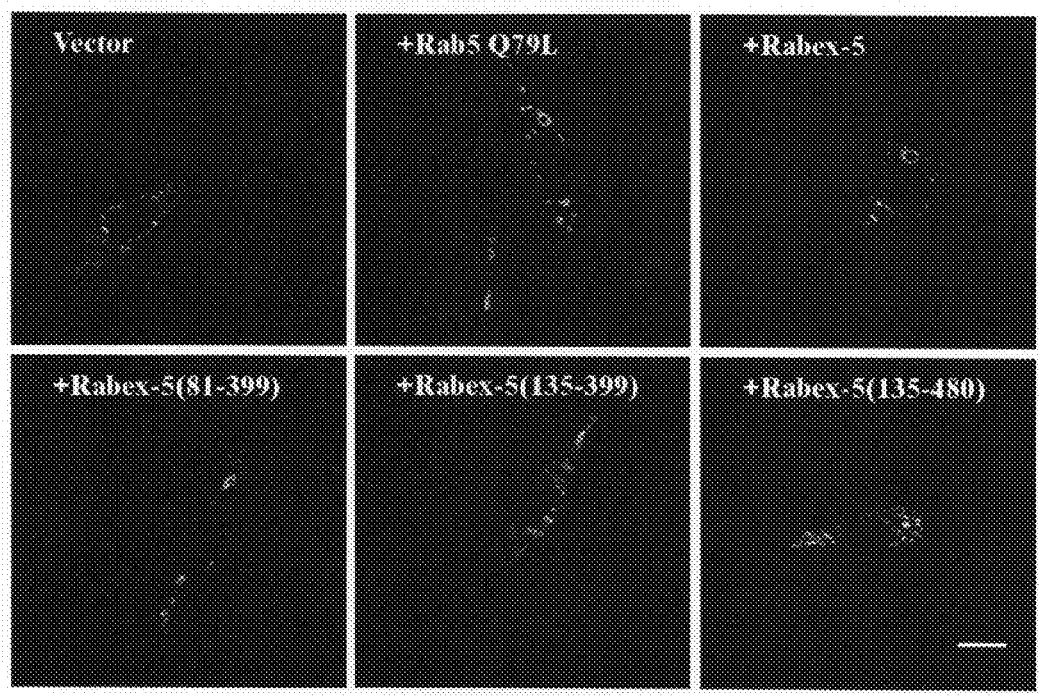
FIG. 18 illustrates the effect of Rabex-5 and truncation mutants on EEA1-positive early endosomes. Confocal fluorescence microscopy images showing the morphological changes of GFP-EEA1-labeled early endosomes in BHK cells co-expressing the indicated Rabex-5 constructs. GFPEEA1 alone (vector) and co-expression with Rab5:Q79L serve as negative and positive controls in determining the enlargement of EEA1-labeled early endosomes. Bar=16 µm.

GFP-Rab5 was expressed to label early endosomes and coexpressed Rabex-5 or various Rabex-5 truncation mutants (FIGS. 13, A and B) to determine whether these Rabex-5 proteins can activate Rab5 and consequently enlarge the early endosomes in BHK cells. This assay was based on previous observations that Rab5 activity in these cells is rate limiting (Bucci et al., 1992; Li and Stahl, 1993). Indeed, the full-length Rabex-5, which has little activity in vitro (Esters et al., 2001; Lippe et al., 2001), exhibited high activity in the cell and led to great enlargement of the Rab5-positive early endosomes, similar to the effect of constitutive active Rab5:Q79L mutant (FIGS. 13, C and 3D). In contrast, Rabex-5(135-399), which is the GEF domain and highly active in vitro (FIG. 12), was inactive in the cell, and it failed to enlarge the early endosomes (FIGS. 13, C and D), indicating that the GEF domain alone cannot activate early endosome-associated Rab5 in the cell. This experiment examined >100 Rabex-5 (135-399)-transfected cells, and none contained the large endosomes seen in Rabex-5-transfected cells, i.e., endosomes with diameter >4 μm. Corroborating the results with the GFP-Rab5-labeled early endosomes, GFP-EEA1-labeled early endosomes were also enlarged by full-length Rabex-5 but not by Rabex-5(135-399) (FIG. 18). The data indicate that the Rabaptin-5-binding domain does not block the GEF activity of Rabex-5 in vivo, in contrast to its negative effect in vitro. Furthermore, endogenous Rabaptin-5 is insufficient to account for the observed Rabex-5 activity in the cell (FIG. 13C; see below).

Figure 19:
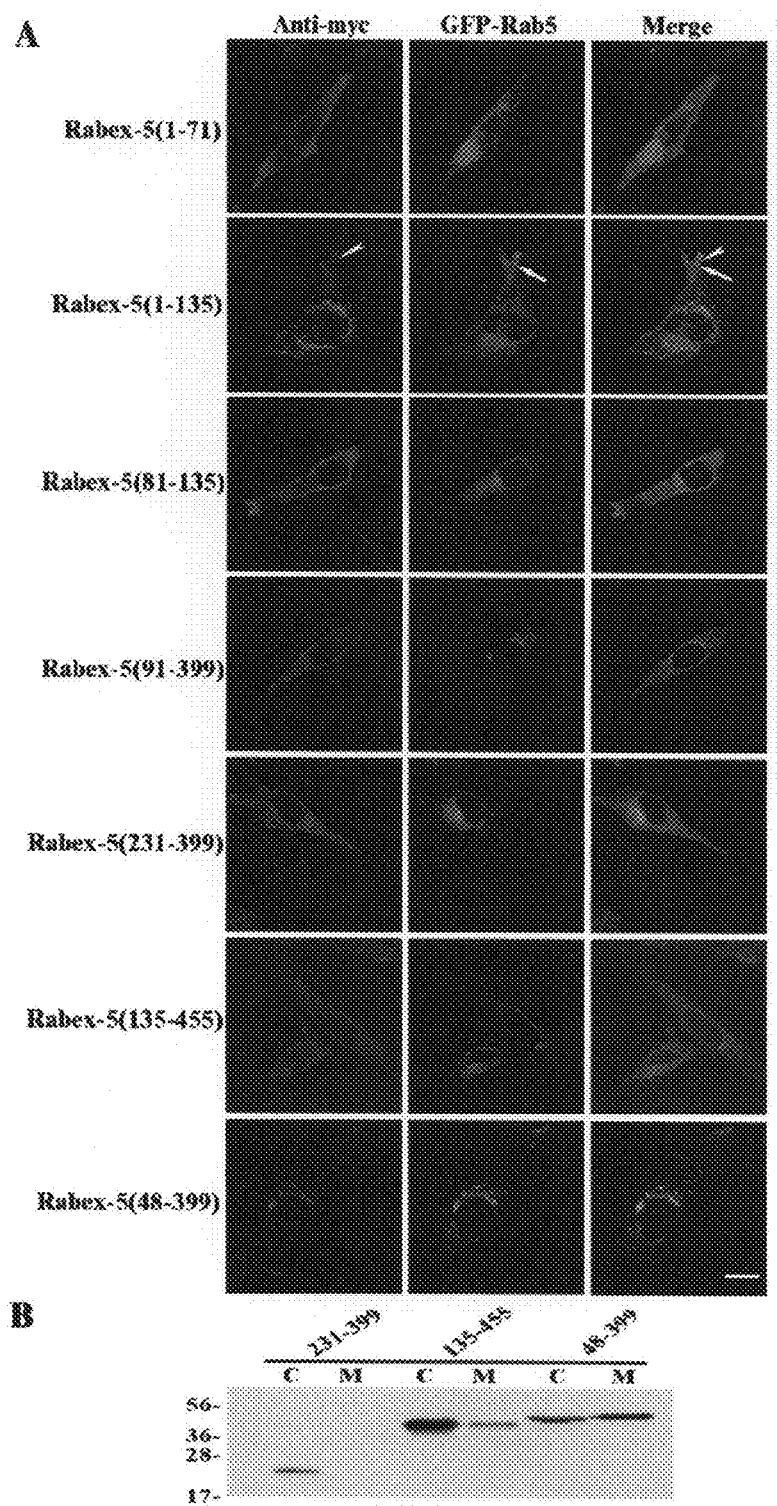
FIG. 19 illustrates that the MBM is necessary but not sufficient for specific targeting to early endosomes. The confocal fluorescence microscopy images show intracellular localization of the indicated Rabex-5 constructs and co-expressed GFP-Rab5 in BHK cells. The Myc-tagged Rabex-5 constructs are identified by indirect immunofluorescence microscopy with the anti-Myc antibody. Bar=16 µm. The bottom panel shows membrane and cytosol distribution of Rabex-5(230-399), Rabex-5(135-455), and Rabex-5(48-399) as indicated. Molecular mass standards (in kDa) are indicated on the left.

The data also indicate that in addition to the core GEF domain, one or more other domains are necessary for Rabex-5 to activate Rab5 in vivo. Several Rabex-5 constructs were made with various combinations of domains (FIG. 13A) to identify regions essential for the GEF activity (FIG. 13C) and the endosomal targeting (FIG. 14) of Rabex-5. To determine whether sequences N terminal to the GEF domain can confer Rab5 GEF activity to Rabex-5(135-399) in the cell, Rabex-5(1-399), Rabex-5(81-399), and Rabex-5(91-399) were expressed in BHK cells (FIG. 13B) to determine their ability in the enlargement of early endosomes. Although Rabex-5(91-399) remained inactive, the two longer N-terminal extension constructs Rabex-5(81-399) and Rabex-5(1-399) were both able to enlarge early endosomes (FIGS. 13, C and D, and FIG. 18), albeit to a lesser extent than full length Rabex-5. Another N-terminal extension construct, Rabex-5 (48-399), also colocalizes with Rab5 on early endosomes, and it was active in enlarging the early endosomes (FIG. 19). Importantly, these active Rabex-5 constructs do not contain the downstream coiled-coil domain involved in Rabaptin-5 binding (residues 401-455), indicating that interaction with Rabaptin-5 is not necessary for Rabex-5 to exhibit Rab5 GEF activity in vivo.

To determine whether sequences C-terminal to the GEF domain, such as the Rabaptin-5-binding domain, may restore the Rab5 GEF activity of Rabex-5(135-399) in vivo, Rabex-5(135-455), Rabex-5(135-480), and Rabex-5(135-492) were made, all of which contained the Rabaptin-5-binding domain with the last one extending all the way to the C terminus. However, like Rabex-5(135-399), Rabex-5(135-480) and Rabex-5(135-492) were inactive in terms of enlarging the early endosomes in BHK cells (FIGS. 13, C and D, and FIG. 18), as was Rabex-5(135-455) (FIG. 19), indicating that endogenous Rabaptin-5 is insufficient to confer activity to these C-terminal extension constructs. Along this line, endogenous Rabaptin-5 is unlikely to contribute to the full-length Rabex-5 activity observed in the cell. Together, the data suggest that Rabex-5 can function independently of Rabaptin-5 in the cell.

Figure 14:
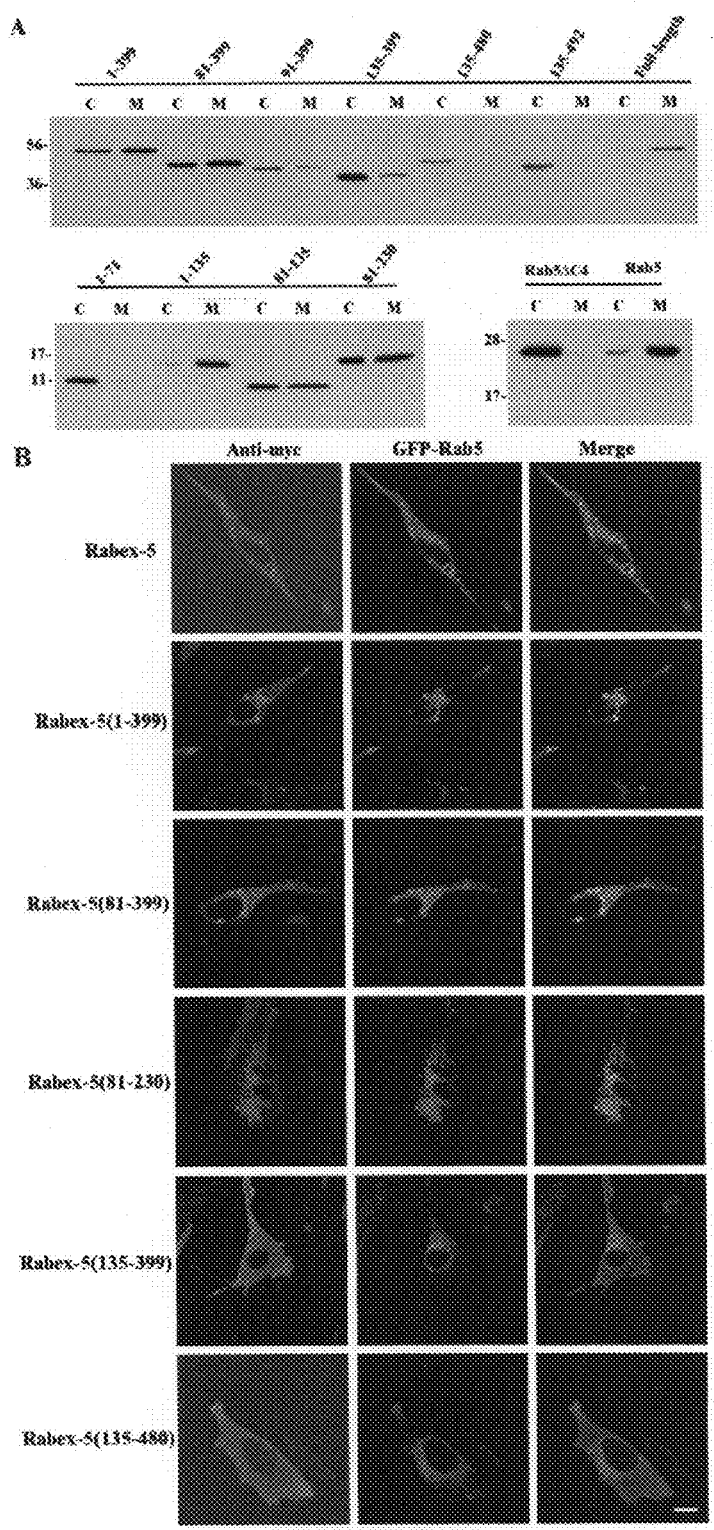
FIG. 14 illustrates that the EET domain necessary and sufficient for early endosomal targeting by Rabex-5. (A) Immunoblot showing the membrane and cytosol distribution of the indicated Rabex-5 constructs, which are schematically illustrated in FIG. 13A. M, membrane; C, cytosol. Molecular mass standards (in kilodaltons) are indicated on the left. (B) Confocal fluorescence microscopy images showing intracellular localization of the indicated Rabex-5 constructs and coexpressed GFP-Rab5 in BHK cells. The Myc-tagged Rabex-5 constructs were identified by indirect immunofluorescence microscopy with the anti-Myc antibody. Bar, 16 μm.

A Novel Early Endosomal Targeting Domain in Rabex-5 Is Essential for Its Rab5 GEF Activity In vivo. To further investigate why the sequence N terminal to the GEF domain is critical for its activity in vivo, the membrane-targeting properties of the aforementioned and additional Rabex-5 constructs was determined, and it was found that the region (residues 81-135) immediately upstream of the GEF domain represents a novel membrane-binding motif (MBM), which together with the downstream helical bundle (HB) domain (residues 135-230) forms a novel early endosomal targeting (EET) domain for Rabex-5 (FIGS. 13A and 14). In the initial experiments, Myc-tagged Rabex-5 fragments were expressed in BHK cells, and cell homogenates were subjected to centrifugation to separate membrane and cytosol fractions. The Rabex-5 proteins in each fraction were identified by immunoblot analysis with an anti-Myc antibody. Full-length Rabex-5 was mostly membrane associated (FIG. 14A). However, Rabex-5(135-399), i.e., the GEF domain, was mostly cytosolic (FIG. 14A), suggesting that its inability to activate Rab5 in vivo may be due to defective membrane targeting. In this regard, all Rabex-5 constructs that showed Rab5 GEF activity in vivo, including Rabex-5(1-399) and Rabex-5(81-399), were also significantly membrane associated, whereas all inactive Rabex-5 constructs, including Rabex-5(135-480), Rabex-5(135-492), and Rabex-5(91-399), shifted toward a mostly cytosolic distribution (FIG. 14A). Thus, there is a general correlation between efficient membrane association of a Rabex-5 construct and its Rab5 GEF activity in vivo. Examination of additional Rabex-5 constructs were consistent with this observation, including the active Rabex-5(48-399) and inactive Rabex-5(135-455) and Rabex-5(230-399), which is the Vps9 domain itself (FIG. 19). Although Rabex-5(135-399) might also interact directly with membrane-bound Rab5, which could account for the residual membrane-bound fraction (☐20%), this direct interaction is apparently too inefficient to activate Rab5 sufficiently and enlarge endosomes in the cell. The membrane/cytosol distribution of additional Rabex-5 constructs lacking the Vps9 domain was also examined, including Rabex-5(1-71) Rabex-5(1-135), Rabex-5(81-135), and Rabex-5(81-230). Rabex-5(1-71), which encompasses the ZnF and UIM domains, was in the cytosol, but Rabex-5(1-135), Rabex-5(81-135), and Rabex-5(81-230) were able to associate with the membrane (FIG. 14A), suggesting that the region encompassing residues 81-135 represents a novel MBM. Rab5 and the Rab5ΔC4 mutant that lacks C-terminal prenylation served as membrane and cytosol controls, respectively (FIG. 14A).

To address more specifically whether the Rabex-5 proteins indeed targeted to Rab5-containing early endosomes, the Myc-tagged Rabex-5 constructs were coexpressed with GFP-Rab5 in BHK cells, and it was determined whether they colocalize with GFP-Rab5 by confocal immunofluorescence microscopy with the anti-Myc antibody. GFP-Rab5-labeled early endosomes, which exhibited a punctate pattern in the cell (FIG. 13C). All Rabex-5 constructs that were able to activate Rab5 in vivo, such as full-length Rabex-5, Rabex-5 (1-399), Rabex-5(81-399), and Rabex-5(48-399), were targeted and colocalized to the GFPRab5-labeled early endosomes, which as a result were generally larger (FIG. 14B and FIG. 19). In contrast, the Rabex-5 constructs that failed to activate Rab5 in vivo, such as the core GEF domain Rabex-5(135-399) and Rabex-5(135-480), showed no detectable colocalization with GFP-Rab5 on the early endosomes (FIG. 14B), neither did Rabex-5(135-455) and Rabex-5(135-492) (FIG. 19). Instead, these inactive Rabex-5 proteins exhibited a diffused cytosolic staining pattern throughout the entire cell (FIG. 14B and FIG. 19).

Figure 20:
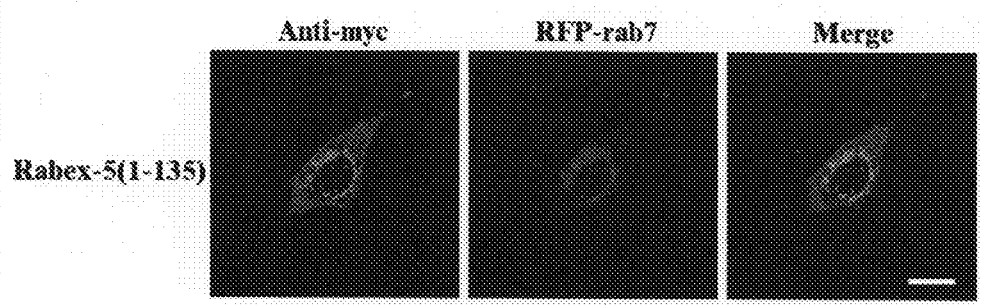
FIG. 20 illustrates the co-localization of Rabex-5(1-135) with Rab7 on late endosomes. Confocal fluorescence microscopy images showing the localization of Rabex-5(1-135) on late endosomes labeled by RFP-Rab7. The Rabex-5(1-135) construct contains Myc-tag and is identified by immunofluorescence microscopy using the anti-Myc antibody. Bar=16 µm.

Importantly, Rabex-5(81-230), which contains the newly identified MBM and HB domains, was sufficient to target to early endosomes and colocalize with Rab5 (FIG. 14B), although the MBM alone [Rabex-5(81-135)] occurred mostly on the plasma membrane (FIG. 19). Rabex-5(1-71) containing the ZnF and UIM domains showed cytosolic distribution (FIG. 19). Interestingly, Rabex-5(1-135) were associated with vesicle-like structures, but these structures were distinct from Rab5-containing endosomes, even though they were occasionally found adjacent to each other (FIG. 19, arrow and arrowhead). Further investigation revealed that Rabex-5(1-135) colocalized with Rab7 on the late endosomes (FIG. 20). Thus, MBM (residues 81-135) represents a novel membrane-binding motif, and they can associate with different membranes in different sequence contexts. Importantly, MBM and the downstream HB domain (residues 135-230) together represent a novel EET domain, which is critical for Rabex-5 to associate with early endosomes and to activate Rab5 in vivo. Because the EET domain lacks the Vps9 domain necessary for interacting with Rab5, it must associate with early endosomes through other early endosomal protein(s) or lipid(s). Phosphatidylinositol 3-phosphate is an important phospholipid involved in recruiting early endosomal proteins, but it seems to not be required for the association of EET domain or Rabex-5 with early endosomes, as evidenced by its insensitivity to wortmannin, a phosphatidylinositol 3-kinase inhibitor (data not shown).

Rabex-5 Can Also Target to Early Endosomes in a Rabaptin-5-dependent Manner In vivo. The expression of Rabex-5 (135-480) and Rabex-5(135-492) constructs both of which contained the Rabaptin-5-binding domain (residues 400-480) did not show any enlargement of early endosomes in the cell (FIG. 13C). However, it was possible that endogenous Rabaptin-5 was limiting. Thus, Rabex-5(135-480) was coexpressed with either full-length Rabaptin-5 or Rabaptin-5(551-661) with the bidirectional vector pBI, which can simultaneously express two proteins on a single plasmid. Indeed, the full-length Rabaptin-5 was able to rescue Rabex-5(135-480) activity in terms of enlargement of GFP-Rab5-labeled early endosomes (FIG. 15A). In contrast, the Rabaptin-5(551-661) fragment was unable to do so (FIG. 15A), even though it formed an active complex with Rabex-5 (135-480) in vitro (FIGS. 11 and 12). Consistent with the recovery of GEF activity, full-length Rabaptin-5 but not Rabaptin-5(551-661) helped Rabex-5(135-480) localize to the Rab5-positive endosomes (FIG. 15B). The expression of Rabaptin-5 and Rabaptin-5(551-661) was further confirmed by immunoblot analysis (FIG. 15C). Because the full-length Rabaptin-5 contains the Rab5-binding domain at the C ter-minus, the results are consistent with previous reports that Rabex-5-Rabaptin-5 complex can target to early endosomes via Rabaptin-5 binding to Rab5-GTP (Lippe et al., 2001; Zhu et al., 2004b).

Figure 16:
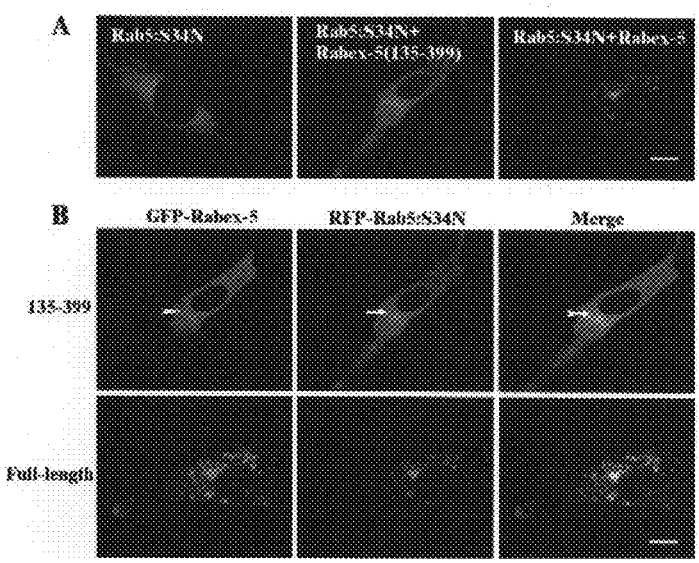
FIG. 16 depicts the rescue of Rab5:S34N-blocked endosome fusion by overexpression of Rabex-5. (A) Confocal fluorescence microscopy images showing the morphology of RFP-Rab5:S34N-labeled early endosomes in BHK cells with or without coexpression of GFP-Rabex-5 or GFP-Rabex-5 (135-399) as indicated. Bar, 16 µm. (B) Confocal fluorescence microscopy images showing localization of GFP-Rabex-5 or GFP-Rabex-5(135-399) in the above-mentioned cells expressing RFP-Rab5:S34N. Arrows indicate partial localization of GFP-Rabex-5(135-399) on RFP-Rab5:S34N endosomes. Bar, 16 µm.

Rabex-5 Can Rescue Rab5:S34N-mediated Inhibition of Early Endosome Fusion. Dominant-negative mutants, such as Rab5:S34N, were suggested to inhibit endogenous Rab5 by sequestration of a Rab5 GEF (Li and Stahl, 1993; Stenmark et al., 1994), but this contention was not formally demonstrated. If endogenous Rabex-5 is the target of sequestration by Rab5:S34N, then overexpression of Rabex-5 should be able to overcome Rab5:S34N-mediated inhibition of early endosome fusion. GFP-Rabex-5 was coexpressed with RFP-Rab5:S34N in BHK cells, and then the morphology of RFP-Rab5:S34N-labeled early endosomes were examined by confocal fluorescence microscopy. Indeed, GFP-Rabex-5 targeted to RFP-Rab5:S34N-labeled early endosomes, and it restored their fusion, as evidenced by the enlargement of RFP-Rab5:S34N-labeled early endosomes in these cells (FIGS. 16, A and B). In control cells without Rabex-5 overexpression, the RFP-Rab5:S34N-labeled endosomes were much smaller, and they accumulated at the perinuclear region (FIG. 16A), due to the inhibition of endosome fusion (Li et al., 1994; Stenmark et al., 1994). Expression of GFP-Rabex-5(135-399), i.e., the GEF domain, did not show any activity to enlarge the Rab5:S34Nlabeled endosomes (FIG. 16A). Although GFP-Rabex-5(135-399) exhibited a mostly diffused cytosolic pattern, a portion of the protein was consistently found on the Rab5:S34N-labeled endosomes (FIG. 16B, arrows). Because Rabex-5(135-399) lacks the EET domain and it is not found on normal early endosomes (FIG. 14B), its partial localization to Rab5:S34N-labeled endosomes is likely due to direct interaction with Rab5:S34N, consistent with the contention that the dominant-negative Rab mutant has higher affinity for and thus can sequester the GEF. The sequestered Rabex-5 (135-399) on the Rab5:S34N-labeled endosomes is apparently inactive, because it cannot activate endogenous Rab5 to enlarge these endosomes (FIG. 16). In this regard, full length Rabex-5 contains the EET domain to mediate its targeting to Rab5:S34N-containing endosomes; thus, it can bypass Rab5:S34N sequestration and retain the ability to activate endogenous Rab5 and enlarge these endosomes (FIG. 16), even though a fraction of Rabex-5 molecules may still bind Rab5:S34N and become sequestered and inactive. That the sequestration occurs on the membrane is consistent with previous findings that the dominant-negative phenotype of Rab5:S34N is dependent on its membrane association and that it can be abolished by truncation of its C-terminal isoprenylation motif (Li et al., 1994).

Discussion

This Example investigates Rabex-5 function in vivo and identifies a direct, Rabaptin-5-independent targeting pathway to early endosomes by Rabex5. Rabex-5 needs to associate with early endosomes first before it can interact effectively with Rab5, and this two-dimensional interaction in the endosomal membrane is not reflected by in vitro nucleotide exchange reactions in solution. For example, the soluble GEF domain itself (residues 135-399) is a potent Rab5 GEF in vitro nucleotide exchange reactions, but it is inactive in the cell in terms of activating Rab5 on the early endosomes. These data strongly suggest that the soluble GEF domain cannot directly act on membrane-bound Rab5-GDP or at least that this interaction is very inefficient, unless it contains additional early endosomal targeting information. The EET domain itself (residues 81-230) is sufficient to target to early endosomes, and it contains a novel MBM (residues 81-135) and the HB domain (residues 135-230). The MBM is not hydrophobic, but it is rich in positively charged residues (10 Lys and 3 Arg), and it is likely to form an amphipathic helix for binding to the membrane, whereas the HB domain may provide specificity via interaction with an early endosome-specific protein or lipid whose nature remains to be investigated. The GEF domain lacks the MBM, and it cannot target to early endosomes efficiently. The two-step mechanism for Rab activation, i.e., GEF targeting to the membrane followed by GEF-Rab interaction, seems conserved in the Rab GTPase family and another well-characterized Rab GEF, Sec2p (the GEF for Sec4p), also contains a membrane-targeting domain necessary for its in vivo function (Elkind et al., 2000).

Figure 15:
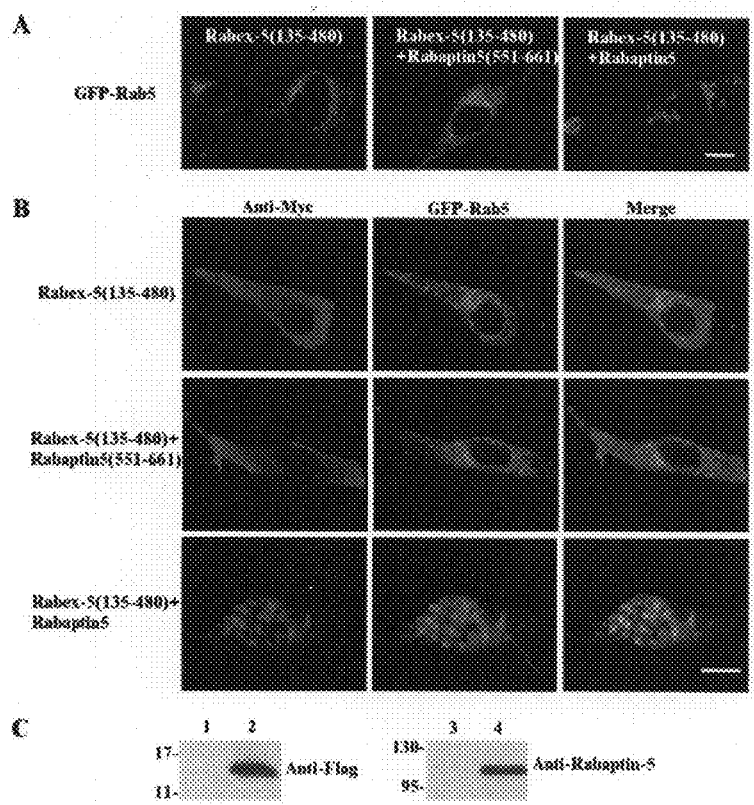
FIG. 15 illustrates Rabaptin-5-mediated Rabex-5 targeting to early endosomes in BHK cells. (A) Confocal fluorescence microscopy images showing the morphology of GFP-Rab5-labeled early endosomes in BHK cells coexpressing Rabex-5(135-480), Rabex-5(135-480)/Rabaptin-5(551-661), or Rabex-5(135-480)/Rabaptin-5, as indicated. Bar, 16 μm. (B) Confocal fluorescence microscopy images showing intracellular localization of GFP-Rab5 and coexpressed Rabex-5(135-480) when expressed alone or together with Rabaptin-5 or Rabaptin-5(551-661), as indicated. The Myc-tagged Rabex-5(135-480) was identified by indirect immunofluorescence microscopy with the anti-Myc antibody. Bar, 16 μm. (C) Immunoblot confirming the coexpression of Rabaptin-5(551-661) that contains a FLAG tag (lane 2) and Rabaptin-5 (lane 4) with the anti-FLAG and anti-Rabaptin-5 antibodies, respectively. Either of the Rabaptin-5 constructs is on the same pBI vector with Myc-Rabex-5(135-480); thus, they are coexpressed with Myc-Rabex-5(135-480) in the same cells as shown in B. The pBI vector that contains only Myc-Rabex-5 (135-480) shows no expression of either FLAG-Rabaptin-5 (551-661) (lane 1) or Rabaptin-5 (lane 3). Molecular mass standards (in kilodaltons) are indicated on the left of each panel.

Rabex-5 efficiently targets to early endosomes and activates Rab5 in the cell, as evidenced by the Rab5-GTP pull-down assay and enlargement of early endosomes. This process does not require interaction with Rabaptin-5, because Rabex-5 truncation mutants lacking the Rabaptin-5-binding domain can target to early endosomes and activate Rab5 in the same manner. Increased Rabex-5 expression can increase Rab5 activity and endosome fusion, suggesting that Rabex-5 level is limiting in these cells. The increased Rabex-5 activity is unlikely to be mediated by Rabaptin-5, because endogenous Rabaptin-5 level is too low and insufficient to form new complexes with the newly expressed Rabex-5 (FIG. 15; see below). In this context, it is necessary to reconcile with previous in vitro data, which show that full-length Rabex-5 has little Rab5 GEF activity in vitro biochemical reactions (Lippe et al., 2001). The results described in FIG. 12 extend this observation and they reveal that the low activity of Rabex-5 in vitro is due to its Rabaptin-5-binding domain. The data are most consistent with the interpretation that the purified Rabex-5 may have a folding/conformational problem in vitro with its active site blocked by the Rabaptin-5-binding domain. Truncation of the Rabaptin-5-binding domain, like binding to Rabaptin-5, can greatly enhance the Rabex-5 GEF activity in vitro. However, in the cell, Rabex-5 has no such folding/conformational problem and it is fully active without Rabaptin-5, although the Rabex-5-Rabaptin-5 complex may play a role in establishing a positive feedback loop to increase rapidly the number of Rab5-GTP molecules in the formation of functional Rab5 domains in the endosomal membranes (Zerial and McBride, 2001; Grosshans et al., 2006).

Rabex-5 specifically targets to early endosomes in the cell, and it is not detected in other intracellular membranes. Rabex-5 can also associate with early endosome preparations in vitro in a Rab5-independent manner, although the in vitro targeting process is rather inefficient in comparison with the Rab5-dependent recruitment of Rabex-5-Rabaptin-5 complex (Lippe et al., 2001). The aforementioned conformational problem may contribute to the inefficient membrane targeting of Rabex-5 in vitro. However, in the cell, Rabex-5 is fully active, and there is no further increase of Rabex-5 activity upon coexpression of Rabaptin-5 (data not shown), suggesting that there is no additive or synergistic effect between the EET and Rabaptin-5-binding domains. Nonetheless, coexpression of Rabaptin-5 can rescue the activity of Rabex-5 (135-480), which itself cannot target to early endosomes because of the truncation of the EET domain, indicating that the Rabaptin-5-mediated Rabex-5 membrane targeting pathway identified in vitro (Lippe et al., 2001) also functions in the cell. In addition, these data suggest that endogenous Rabaptin-5 is already in complexes with endogenous Rabex-5 and/or other proteins and that it is unavailable to form new complexes.

Figure 17:
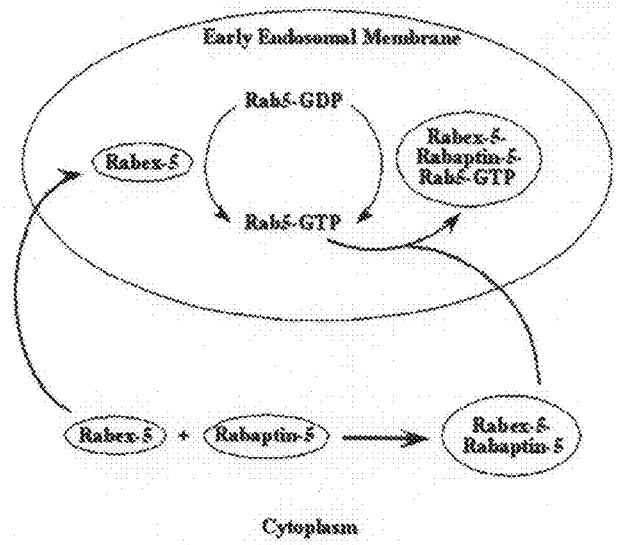
FIG. 17 depicts a model on direct and indirect membrane targeting and Rab5 activation by Rabex-5. Rabex-5 targets to the early endosomal membrane in two parallel pathways: direct targeting via the EET domain identified in this report and indirect targeting via Rabaptin-5-mediated binding to Rab5-GTP described previously (Lippe et al., 2001). Direct targeting of Rabex-5 is necessary to promote the production of a basal level of Rab5-GTP, which in turn recruits Rabaptin-5-Rabex-5 complexes to the endosomal membrane to convert more Rab5-GDP to Rab5-GTP. This effectively creates a positive feedback loop to accumulate Rab5-GTP molecules on the membrane, leading to the establishment of functional Rab5 domains.

Thus, there are two parallel pathways for Rabex-5 to associate with early endosomes: direct targeting via the EET domain and indirect targeting via Rabaptin-5 binding to Rab5-GTP (FIG. 17). Direct targeting may account for most of the membrane-associated pool of Rabex-5, whereas Rabaptin-5 determines the cytosolic pool of Rabex-5, taken into consideration that Rabex-5 was originally isolated as a soluble Rabex-5-Rabaptin-5 complex (Horiuchi et al., 1997), and there is little free Rabex-5 in the cytosol (Lippe et al., 2001). Interestingly, Rabaptin-5 binding to Rabex-5 seems to block the direct membrane targeting pathway, possibly by masking the EET domain, because the Rabex-5-Rabaptin-5 complex either remains in the cytosol or targets to early endosomes in a Rab5-dependent manner via Rabaptin-5 binding to Rab5-GTP (Lippe et al., 2001; Zhu et al., 2004b). Because the intrinsic exchange rate from Rab5-GDP to Rab5-GTP is extremely low, an apparent advantage of direct targeting is to provide a basal level of Rabex-5 on early endosomal membranes, which in turn produces a basal level of Rab5-GTP. In this context, the cytosolic Rabex-5-Rabaptin-5 complex can function via binding to Rab5-GTP and targeting to early endosomes, which forms a positive feedback loop to produce more Rab5-GTP and consequently establish a functional Rab5 domain in the endosomal membrane (Zerial and McBride, 2001; Grosshans et al., 2006).

Thus, in accordance with the present invention, there has been provided methods of determining intracellular Rab5 activity that fully satisfies the objectives and advantages set forth hereinabove. Although the invention has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the invention.

REFERENCES

The following references, to the extent that they provide exemplary procedural or other details supplementary to those set forth herein, are specifically incorporated herein by reference.

Bivona, T. G., Perez De Castro, I., Ahearn, I. M., Grana, T. M., Chiu, V. K., Lockyer, P. J., Cullen, P. J., Pellicer, A., Cox, A. D., and Philips, M. R. (2003). Phospholipase Cgamma activates Ras on the Golgi apparatus by means of RasGRP1. Nature 424, 694-698.

Bucci, C., Parton, R. G., Mather, I. M., Stunnenberg, H., Simons, K., Hoflack, B., and Zerial, M. (1992). The small GTPase Rab5 functions as a regulatory factor in the early endocytic pathway. Cell 70, 715-728.

Carney, D. S., Davies, B. A., and Horazdovsky, B. F. (2006). Vps9 domaincontaining proteins: activators of Rab5 GTPases from yeast to neurons. Trends Cell Biol. 16, 27-35.

Ceresa, B. P., and Schmid, S. L. (2000). Regulation of signal transduction by endocytosis. Curr. Opin. Cell Biol. 12, 204-210.

Delcroix, J. D., Valletta, J. S., Wu, C., Hunt, S. J., Kowal, A. S., and Mobley, W. C. (2003). NGF signaling in sensory neurons: evidence that early endosomes carry NGF retrograde signals. Neuron 39, 69-84.

Delcroix, J. D., Valletta, J., Wu, C., Howe, C. L., Lai, C. F., Cooper, J. D., Belichenko, P. V., Salehi, A., and Mobley, W. C. (2004). Trafficking the NGF signal: implications for normal and degenerating neurons. Prog. Brain Res. 146, 3-23.

Delprato, A., and Lambright, D. G. (2007). Structural basis for Rab GTPaes activation by VPS9 domain exchange factors. Nat. Struct. Mol. Biol. 14, 406-412.

Delprato, A., Merithew, E., and Lambright, D. G. (2004). Structure, exchange determinants, and family-wide rab specificity of the tandem helical bundle and Vps9 domains of Rabex-5. Cell 118, 607-617.

Elkind, N. B., Walch-Solimena, C., and Novick, P. J. (2000). The role of the COOH terminus of Sec2p in the transport of post-Golgi vesicles. J. Cell Biol. 149, 95-110.

Esters, H., Alexandrov, K., Iakovenko, A., Ivanova, T., Thoma, N., Rybin, V., Zerial, M., Scheidig, A. J., and Goody, R. S. (2001). Vps9, Rabex-5 and DSS 4, proteins with weak but distinct nucleotide-exchange activities for Rab proteins. J. Mol. Biol. 310, 141-156.

Gorvel, J.-P., Chavrier, P., Zerial, M., and Gruenberg, J. (1991). rab5 controls early endosome fusion in vitro. Cell 64, 915-925.

Greene, L. A., and Tischler, A. S. (1976). Establishment of a noradrenergic clonal line of rat adrenal pheochromocytoma cells which respond to nerve growth factor. Proc. Natl. Acad. Sci. USA 73, 2424-2428.

Grimes, M. L., Zhou, J., Beattie, E. C., Yuen, E. C., Hall, D. E., Vallefta, J. S., Topp, K. S., LaVail, J. H., Bunneft, N. W., and Mobley, W. C. (1996). Endocytosis of activated TrkA: evidence that nerve growth factor induces formation of signaling endosomes. J. Neurosci. 16, 7950-7964.

Grosshans, B. L., Ortiz, D., and Novick, P. (2006). Rabs and their effectors: achieving specificity in membrane traffic. Proc. Natl. Acad. Sci. USA 103, 11821-11827.

Haas, A. K., Fuchs, E., Kopajtich, R., and Barr, F. A. (2005). A GTPaseactivating protein controls Rab5 function in endocytic trafficking. Nat. Cell Biol. 7, 887-893.

Hoffenberg, S., Sanford, J. C., Liu, S., Daniel, D. S., Tuvin, M., Knoll, B. J., Wessling-Resnick, M., and Dickey, B. F. (1995). Biochemical and functional characterization of a recombinant GTPase, Rab5, and two of its mutants. J. Biol. Chem. 270, 5048-5056.

Horiuchi, H. et al. (1997). A novel Rab5 GDP/GTP exchange factor complexed to Rabaptin-5 links nucleotide exchange to effector recruitment and function. Cell 90, 1149-1159.

Howe, C. L., and Mobley, W. C. (2004). Signaling endosome hypothesis: a cellular mechanism for long distance communication. J. Neurobiol. 58, 207-216.

Huang, E. J., and Reichardt, L. F. (2001). Neurotrophins: roles in neuronal development and function. Annu. Rev. Neurosci. 24, 677-736.

Jullien, J., Guili, V., Reichardt, L. F., and Rudkin, B. B. (2002). Molecular kinetics of nerve growth factor receptor trafficking and activation. J. Biol. Chem. 277, 38700-38708.

Kajiho, H., Saito, K., Tsujita, K., Kontani, K., Araki, Y., Kurosu, H., and Katada, T. (2003). RIN 3, a novel Rab5 GEF interacting with amphiphysin 11 involved in the early endocytic pathway. J. Cell Sci. 116, 4159-4168.

Kalesnikoff, J., Rios, E. J., Chen, C. C., Nakae, S., Zabel, B. A., Butcher, E. C., Tsai, M., Tam, S. Y., and Galli, S. J. (2006). RabGEF1 regulates stem cell factor/c-Kit-mediated signaling events and biological responses in mast cells. Proc. Natl. Acad. Sci. USA 103, 2659-2664.

Lanzetti, L., Palamidessi, A.; Areces, L., Scita, G., and Di Fiore, P. P. (2004). Rab5 is a signalling GTPase involved in actin remodelling by receptor tyrosine kinases. Nature 429, 309-314.

Lanzetti, L., Rybin, V., Malabarba, M. G., Christoforidis, S., Scita, G., Zerial, M., and Di Fiore, P. P. (2000). The Eps8 protein coordinates EGF receptor signalling through Rac and trafficking through Rab5. Nature 408, 374-377.

Lee, S., Tsai, Y. C., Mattera, R., Smith, W. J., Kostelansky, M. S., Weissman, A. M., Bonifacino, J. S., and Hurley, J. H. (2006). Structural basis for ubiquitin recognition and autoubiquitination by Rabex-5. Nat. Struct. Mol. Biol. 13, 264-271.

Li, G., and Liang, Z. (2001). Phosphate-binding loop and Rab GTPase function: mutations at Ser29 and Ala30 of Rab5 lead to loss-of-function as well as gain-of-function phenotype. Biochem. J. 355, 681-689.

Li, G., and Stahl, P. D. (1993). Structure-function relationship of the small GTPase Rab5. J. Biol. Chem. 268, 24475-24480.

Li, G., Barbieri, M. A., Colombo, M. I., and Stahl, P. D. (1994). Structural features of the GTP-binding defective Rab5 mutants required for their inhibitory activity on endocytosis. J. Biol. Chem. 269, 14631-14635.

Liang, Z., Mather, T., and Li, G. (2000). GTPase mechanism and function: new insights from systematic mutational analysis of the phosphate-binding loop residue Ala30 of Rab5. Biochem. J. 346, 501-508.

Lippe, R., Miaczynska, M., Rybin, V., Runge, A., and Zerial, M. (2001). Functional synergy between Rab5 effector Rabaptin-5 and exchange factor Rabex-5 when physically associated in a complex. Mol. Biol. Cell 12, 2219-2228.

Mattera, R., Tsai, Y. C., Weissman, A. M., and Bonifacino, J. S. (2006). The Rab5 guanine nucleotide exchange factor Rabex-5 binds ubiquitin (Ub) and functions as a Ub ligase through an atypical Ub-interacting motif and a zinc finger domain. J. Biol. Chem. 281, 6874-6883.

Meakin, S. O., MacDonald, J. I., Gryz, E. A., Kubu, C. J., and Verdi, J. M. (1999). The signaling adapter FRS-2 competes with Shc for binding to the nerve growth factor receptor TrkA. A model for discriminating proliferation and differentiation. J. Biol. Chem. 274, 9861-9870.

Mochizuki, N., Yamashita, S., Kurokawa, K., Ohba, Y., Nagai, T., Miyawaki, A., and Matsuda, M. (2001). Spatiotemporal images of growth-factor-induced activation of Ras and Rap1. Nature 411, 1065-1068.

Nosaka, Y., Arai, A., Miyasaka, N., and Miura, O. (1999). CrkL mediates Ras-dependent activation of the Raf/ERK pathway through the guanine nucleotide exchange factor C3G in hematopoietic cells stimulated with erythropoietin or interleukin-3. J. Biol. Chem. 274, 30154-30162.

Penengo, L., Mapelli, M., Murachelli, A. G., Confalonieri, S., Magri, L., Musacchio, A., Di Fiore, P. P., Polo, S., and Schneider, T. R. (2006). Crystal structure of the ubiquitin binding domains of rabex-5 reveals two modes of interaction with ubiquitin. Cell 124, 1183-1195.

Rink, J., Ghigo, E., Kalaidzidis, Y., and Zerial, M. (2005). Rab conversion as a mechanism of progression from early to late endosomes. Cell 122, 735-749.

Rybin, V., Ulirich, O., Rubino, M., Alexandrov, K., Simon, I., Seabra, M. C., Goody, R., and Zerial, M. (1996). GTPase activity of Rab5 acts as a timer for endocytic membrane fusion. Nature 383, 266-269.

Saito, K., Murai, J., Kajiho, H., Kontani, K., Kurosu, H., and Katada, T. (2002). A novel binding protein composed of homophilic tetramer exhibits unique properties for the small GTPase Rab5. J. Biol. Chem. 277, 3412-3418.

Segal, R. A. (2003). Selectivity in neurotrophin signaling: theme and variations. Annu. Rev. Neurosci. 26, 299-330.

Stenmark, H., Parton, R. G., Steele-Mortimer, O., Lutcke, A., Gruenberg, J., and Zerial, M. (1994). Inhibition of rab5 GTPase activity stimulates membrane fusion in endocytosis. EMBO J. 13, 1287-1296.

Stenmark, H., Vitale, G., Ullrich, O., and Zerial, M. (1995). Rabaptin-5 is a direct effector of the small GTPase Rab5 in endocytic membrane fusion. Cell 83, 423-432.

Tall, G. G., Barbieri, M. A., Stahl, P. D., and Horazdovsky, B. F. (2001). Ras-activated endocytosis is mediated by the Rab5 guanine nucleotide exchange activity of RIN1. Dev. Cell 1, 73-82.

Tam, S. Y., Tsai, M., Snouwaert, J. N., Kalesnikoff, J., Scherrer, D., Nakae, S., Chatterjea, D., Bouley, D. M., and Galli, S. J. (2004). RabGEF1 is a negative regulator of mast cell activation and skin inflammation. Nat. Immunol. 5, 844-852.

Ullrich, O., Horiuchi, H., Bucci, C., and Zerial, M. (1994). Membrane association of Rab5 mediated by GDP-dissociation inhibitor and accompanied by GDP/GTP exchange. Nature 368, 157-160.

Xiao, G. H., Shoarinejad, F., Jin, F., Golemis, E. A., and Yeung, R. S. (1997). The tuberous sclerosis 2 gene product, tuberin, functions as a Rab5 GTPase activating protein (GAP) in modulating endocytosis. J. Biol. Chem. 272, 6097-6100.

York, R. D., Molliver, D. C., Grewal, S. S., Stenberg, P. E., McCleskey, E. W., and Stork, P. J. (2000). Role of phosphoinositide 3-kinase and endocytosis in nerve growth factor-induced extracellular signal-regulated kinase activation via Ras and Rap1. Mol. Cell Biol. 20, 8069-8083.

York, R. D., Yao, H., Dillon, T., Ellig, C. L., Eckert, S. P., McCleskey, E. W., and Stork, P. J. (1998). Rap1 mediates sustained MAP kinase activation induced by nerve growth factor. Nature 392, 622-626.

Zerial, M., and McBride, H. (2001). Rab proteins as membrane organizers. Nat. Rev. Mol. Cell Biol. 2, 107-117.

Zhang, Y., Moheban, D. B., Conway, B. R., Bhattacharyya, A., and Segal, R. A. (2000). Cell surface Trk receptors mediate NGF-induced survival while internalized receptors regulate NGF-induced differentiation. J. Neurosci. 20, 5671-5678.

Zhou, J., Valletta, J. S., Grimes, M. L., and Mobley, W. C. (1995). Multiple levels for regulation of TrkA in PC12 cells by nerve growth factor. J. Neurochem. 65, 1146-1156.

Zhu, G., Zhai, P., He, X., Wakeham, N., Rodgers, K., Li, G., Tang, J., and Zhang, X. C. (2004a). Crystal structure of human GGA1 GAT domain complexed with the GAT-binding domain of Rabaptin5. EMBO J. 23, 3909-3917.

Zhu, G., Zhai, P., Liu, J., Terzyan, S., Li, G., and Zhang, X. C. (2004b). Structural basis of Rab5-Rabaptin5 interaction in endocytosis. Nat. Struct. Mol. Biol. 11, 975-983.

---

What is claimed is:

1. A method of determining intracellular Rab5 activity in a cell sample, comprising the steps of:
   providing a fusion protein, wherein the fusion protein comprises a Rab5-binding domain that specifically binds to an activated form of Rab5-GTP, and a tag conjugated thereto, wherein the tag is capable of binding to an affinity matrix for purification of Rab5-GTP;
   contacting the fusion protein with an affinity matrix or resin containing a molecule to which the tag of the fusion protein specifically binds;
   contacting a cell lysate with the fusion protein bound to the affinity matrix or resin such that Rab5-GTP present in the cell lysate will specifically bind to the fusion protein, thus forming a complex;
   rinsing the complex to remove the cell lysate; and
   determining the amount of Rab5-GTP present in the complex.

2. The method of claim 1, wherein the step of determining the amount of Rab5-GTP present in the complex is further defined as subjecting the complex to gel electrophoresis followed by immunoblot analysis with an anti-Rab5 antibody.

3. The method of claim 1, further comprising the step of determining an amount of total Rab5 present in the cell sample.

4. The method of claim 1 wherein, in the step of providing a fusion protein, the Rab5-binding domain comprises at least a portion of a Rab5 effector protein selected from the group consisting of Rabaptin-5, EEA1(early endosome autoantigen), APPL1 and APPL2 (adaptor protein containing PH domain, PTB domain, and Leucine zipper motif 1 or 2), and Rabenosyn-5.

5. The method of claim 1 wherein, in the step of providing a fusion protein, the Rab5-binding domain comprises at least one of SEQ ID NOS:1-3.

6. The method of claim 1 wherein, in the step of providing a fusion protein, the tag comprises at least one of SEQ ID NOS:4-6.

7. The method of claim 1 wherein, in the step of contacting the fusion protein with a matrix or resin, the matrix or resin is selected from the group consisting of glutathione, nickel, zinc, amylase, agarose beads, and combinations thereof.

8. A method of determining intracellular Rab5 activity in a cell sample, comprising the steps of:
   providing a fusion protein, wherein the fusion protein comprises a Rab5-binding domain that specifically binds to an activated form of Rab5-GTP, and a tag conjugated thereto, wherein the tag is capable of binding to an affinity matrix for purification of Rab5-GTP;
   contacting the fusion protein with an affinity matrix or resin containing a molecule to which the tag of the fusion protein specifically binds;
   immobilizing the affinity matrix or resin having the fusion protein bound thereto on a solid support;
   contacting a cell lysate with the immobilized fusion protein such that Rab5-GTP present in the cell lysate will specifically bind to the immobilized fusion protein;
   eluting the Rab5-GTP from the solid support with an elution buffer; and
   determining the amount of Rab5-GTP present in the in the collected elution buffer.

9. The method of claim 8, wherein the step of determining the amount of Rab5-GTP present in the collected elution buffer is further defined as subjecting the mixture to gel electrophoresis followed by immunoblot analysis with an anti-Rab5 antibody.

10. The method of claim 8, further comprising the step of determining an amount of total Rab5 present in the cell sample.

11. The method of claim 8 wherein, in the step of providing a fusion protein, the Rab5-binding domain comprises at least a portion of a Rab5 effector protein selected from the group consisting of Rabaptin-5, EEA1 (early endosome autoantigen), APPL1 and APPL2 (adaptor protein containing PH domain, PTB domain, and Leucine zipper motif 1 or 2), and Rabenosyn-5.

12. The method of claim 8 wherein, in the step of providing a fusion protein, the Rab5-binding domain comprises at least one of SEQ ID NOS:1-3.

13. The method of claim 8 wherein, in the step of providing a fusion protein, the tag comprises at least one of SEQ ID NOS:4-6.

14. The method of claim 8 wherein, in the step of providing a fusion protein, the affinity matrix is selected from the group consisting of glutathione, nickel, zinc, amylase, agarose beads, and combinations thereof.

* * * * *

UNITED STATES PATENT AND TRADEMARK OFFICE
CERTIFICATE OF CORRECTION

PATENT NO. : 7,838,249 B2
APPLICATION NO. : 11/998244
DATED : November 23, 2010
INVENTOR(S) : Guangpu Li It is certified that error appears in the above-identified patent and that said Letters Patent is hereby corrected as shown below:

Column 9, line 42: After "(i)" delete IIe" and replace with -- Ile --.

Column 9, line 43: Delete "GIn," and replace with -- Gln, --.

Column 19, line 18: Delete "MluI" and replace with -- MluI --.

Column 19, line 26: Delete "MluI" and replace with -- MluI --.

Column 21, lines 49-50: Delete "5'-GGCCCTATTTGMCATGGA-3'" and replace with

-- 5'-GGCCCTATTTGAACATGGA-3' --.

Column 29, line 5: After "activity" insert -- in --.

Column 30, line 24: Delete "supermatant" and replace with -- supernatant --.

Column 31, line 42: Delete "(wUv)." and replace with -- (wt/v). --.

Column 37, line 9: After "potent Rab4 GEF" insert -- in --.

Column 37, line 45: After "GEF activity" insert -- in --.

Column 39, line 40: Delete "Vallefta," and replace with -- Valletta, -- and delete "Bunneft,"

and replace with -- Bunnett, --.

Column 40, line 3: After "amphiphysin" delete "1 1" and replace with -- II--.

Column 40, line 9: Delete "NatI." and replace with -- Natl. --.

Column 41, line 4: Delete "Ulirich," and replace with -- Ullrich, --.

Signed and Sealed this
Fifth Day of April, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,838,249 B2 | Page 1 of 1 |
| APPLICATION NO. | : 11/998244 | |
| DATED | : November 23, 2010 | |
| INVENTOR(S) | : Guangpu Li | |

It is certified that error appears in the above-identified patent and that said Letters Patent is hereby corrected as shown below:

In the Specification

On Column 1, line 14, please delete 'Not Applicable.' and replace with:
This invention was made with government support under Contract Number GM074692 awarded by the National Institutes of Health (NIH). The government has certain rights in the invention.

Signed and Sealed this
Fourth Day of February, 2014

Michelle K. Lee
*Deputy Director of the United States Patent and Trademark Office*

SEQUENCE LISTING

```
<160> NUMBER OF SEQ ID NOS: 11

<210> SEQ ID NO 1
<211> LENGTH: 124
<212> TYPE: PRT
<213> ORGANISM: Homo sapiens

<400> SEQUENCE: 1

Ala Ser Ile Ser Ser Leu Lys Ala Glu Leu Glu Arg Ile Lys Val Glu
1               5                   10                  15

Lys Gly Gln Leu Glu Ser Thr Leu Arg Glu Lys Ser Gln Gln Leu Glu
            20                  25                  30

Ser Leu Gln Glu Ile Lys Ile Ser Leu Glu Glu Gln Leu Lys Lys Glu
        35                  40                  45

Thr Ala Ala Lys Ala Thr Val Glu Gln Leu Met Phe Glu Glu Lys Asn
    50                  55                  60

Lys Ala Gln Arg Leu Gln Thr Glu Leu Asp Val Ser Glu Gln Val Gln
65                  70                  75                  80

Arg Asp Phe Val Lys Leu Ser Gln Thr Leu Gln Val Gln Leu Glu Arg
                85                  90                  95

Ile Arg Gln Ala Asp Ser Leu Glu Arg Ile Arg Ala Ile Leu Asn Asp
                100                 105                 110

Thr Lys Leu Thr Asp Ile Asn Gln Leu Pro Glu Thr
            115                 120
```

<210> SEQ ID NO 2
<211> LENGTH: 72
<212> TYPE: PRT
<213> ORGANISM: Homo sapiens

<400> SEQUENCE: 2

Ala Thr Val Glu Gln Leu Met Phe Glu Glu Lys Asn Lys Ala Gln Arg
1               5                   10                  15

Leu Gln Thr Glu Leu Asp Val Ser Glu Gln Val Gln Arg Asp Phe Val
            20                  25                  30

Lys Leu Ser Gln Thr Leu Gln Val Gln Leu Glu Arg Ile Arg Gln Ala
        35                  40                  45

Asp Ser Leu Glu Arg Ile Arg Ala Ile Leu Asn Asp Thr Lys Leu Thr
    50                  55                  60

Asp Ile Asn Gln Leu Pro Glu Thr
65                  70

<210> SEQ ID NO 3
<211> LENGTH: 209
<212> TYPE: PRT
<213> ORGANISM: Homo sapiens

<400> SEQUENCE: 3

Met Leu Arg Arg Ile Leu Gln Arg Thr Pro Gly Arg Val Gly Ser Gln
1               5                   10                  15

Gly Ser Asp Leu Asp Ser Ser Ala Thr Pro Ile Asn Thr Val Asp Val
            20                  25                  30

Asn Asn Glu Ser Ser Glu Gly Phe Ile Cys Pro Gln Cys Met Lys
        35                  40                  45

Ser Leu Gly Ser Ala Asp Glu Leu Phe Lys His Tyr Glu Ala Val His
    50                  55                  60

Asp Ala Gly Asn Asp Ser Gly His Gly Gly Glu Ser Asn Leu Ala Leu
65                  70                  75                  80

Lys Arg Asp Asp Val Thr Leu Leu Arg Gln Glu Val Gln Asp Leu Gln
                85                  90                  95

Ala Ser Leu Lys Glu Glu Lys Trp Tyr Ser Glu Leu Lys Lys Glu
            100                 105                 110

Leu Glu Lys Tyr Gln Gly Leu Gln Gln Gln Ala Lys Pro Asp Gly
        115                 120                 125

Leu Val Thr Asp Ser Ser Ala Glu Leu Gln Ser Leu Glu Gln Gln Leu
    130                 135                 140

Glu Glu Ala Gln Thr Glu Asn Phe Asn Ile Lys Gln Met Lys Asp Leu
145                 150                 155                 160

Phe Glu Gln Lys Ala Ala Gln Leu Ala Thr Glu Ile Ala Asp Ile Lys
                165                 170                 175

Ser Lys Tyr Asp Glu Glu Arg Ser Leu Arg Glu Ala Ala Glu Gln Lys
            180                 185                 190

Val Thr Arg Leu Thr Glu Glu Leu Asn Lys Glu Ala Thr Val Ile Gln
        195                 200                 205

Asp

<210> SEQ ID NO 4
<211> LENGTH: 231
<212> TYPE: PRT
<213> ORGANISM: Artificial Sequence
<220> FEATURE:
<223> OTHER INFORMATION: glutathione-S-transferase epitope, from cloning
      vectors

```
<400> SEQUENCE: 4

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Ile Glu Gly
    210                 215                 220

Arg Gly Ile Pro Gly Asn Ser
225                 230

<210> SEQ ID NO 5
<211> LENGTH: 6
<212> TYPE: PRT
<213> ORGANISM: Artificial Sequence
<220> FEATURE:
<223> OTHER INFORMATION: 6His epitope

<400> SEQUENCE: 5

His His His His His His
1               5

<210> SEQ ID NO 6
<211> LENGTH: 368
<212> TYPE: PRT
<213> ORGANISM: Artificial Sequence
<220> FEATURE:
<223> OTHER INFORMATION: Maltose Binding Protein epitope, from cloning
      vectors

<400> SEQUENCE: 6

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
```

```
                35                  40                  45
Pro Gln Val Ala Ala Thr Gly Asp Gly Pro Asp Ile Ile Phe Trp Ala
 50                  55                  60
His Asp Arg Phe Gly Gly Tyr Ala Gln Ser Gly Leu Leu Ala Glu Ile
 65                  70                  75                  80
Thr Pro Asp Lys Ala Phe Gln Asp Lys Leu Tyr Pro Phe Thr Trp Asp
                 85                  90                  95
Ala Val Arg Tyr Asn Gly Lys Leu Ile Ala Tyr Pro Ile Ala Val Glu
            100                 105                 110
Ala Leu Ser Leu Ile Tyr Asn Lys Asp Leu Leu Pro Asn Pro Pro Lys
        115                 120                 125
Thr Trp Glu Glu Ile Pro Ala Leu Asp Lys Glu Leu Lys Ala Lys Gly
130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
            180                 185                 190
Leu Thr Phe Leu Val Asp Leu Ile Lys Asn Lys His Met Asn Ala Asp
        195                 200                 205
Thr Asp Tyr Ser Ile Ala Glu Ala Ala Phe Asn Lys Gly Glu Thr Ala
210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
            260                 265                 270
Asn Lys Glu Leu Ala Lys Glu Phe Leu Glu Asn Tyr Leu Leu Thr Asp
        275                 280                 285
Glu Gly Leu Glu Ala Val Asn Lys Asp Lys Pro Leu Gly Ala Val Ala
290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
            340                 345                 350
Ser Gly Arg Gln Thr Val Asp Glu Ala Leu Lys Asp Ala Gln Thr Asn
        355                 360                 365

<210> SEQ ID NO 7
<211> LENGTH: 21
<212> TYPE: DNA
<213> ORGANISM: Rattus norvegicus

<400> SEQUENCE: 7
gcatctggga cctgttcttc t                                           21

<210> SEQ ID NO 8
<211> LENGTH: 21
<212> TYPE: DNA
<213> ORGANISM: Rattus norvegicus

<400> SEQUENCE: 8
```

```
-continued gccctatttg aacatggatt g                                                    21

<210> SEQ ID NO 9
<211> LENGTH: 19
<212> TYPE: DNA
<213> ORGANISM: Rattus norvegicus

<400> SEQUENCE: 9
ggcaaagaac atcaaacaa                                                       19

<210> SEQ ID NO 10
<211> LENGTH: 19
<212> TYPE: DNA
<213> ORGANISM: Rattus norvegicus

<400> SEQUENCE: 10
ggccctattt gaacatgga                                                       19

<210> SEQ ID NO 11
<211> LENGTH: 21
<212> TYPE: DNA
<213> ORGANISM: Homo sapiens

<400> SEQUENCE: 11
gcagagcaac cagagttcta c                                                    21
```